(12) United States Patent
Ellingwood

(10) Patent No.: US 8,556,930 B2
(45) Date of Patent: Oct. 15, 2013

(54) VESSEL CLOSURE DEVICE

(75) Inventor: Brian A. Ellingwood, Sunnyvale, CA (US)

(73) Assignee: Abbott Laboratories, Abbott Park, IL (US)

(*) Notice: Subject to any disclaimer, the term of this patent is extended or adjusted under 35 U.S.C. 154(b) by 806 days.

(21) Appl. No.: 11/427,309

(22) Filed: Jun. 28, 2006

(65) Prior Publication Data

US 2008/0004640 A1    Jan. 3, 2008

(51) Int. Cl.
*A61B 17/08* (2006.01)
*A61B 17/64* (2006.01)

(52) U.S. Cl.
USPC .............................. 606/213; 606/139; 606/151

(58) Field of Classification Search
USPC ............... 606/151, 213, 139, 142, 144, 148, 606/153–154, 157–158; 29/240.5
See application file for complete search history.

(56) References Cited

U.S. PATENT DOCUMENTS

| | | | |
|---|---|---|---|
| 287,046 A | 10/1883 | Norton | |
| 438,400 A | 10/1890 | Brennen | |
| 556,082 A * | 3/1896 | Boeddinghaus | 52/705 |
| 1,088,393 A | 2/1914 | Backus | |
| 1,242,139 A | 10/1917 | Callahan | |
| 1,331,401 A | 2/1920 | Summers | |
| 1,480,935 A | 1/1924 | Gleason | |
| 1,596,004 A | 8/1926 | De Bengoa | |
| 1,647,958 A | 11/1927 | Ciarlante | |
| 1,880,569 A | 10/1932 | Weis | |
| 2,087,074 A | 7/1937 | Tucker | |
| 2,210,061 A * | 8/1940 | Caminez | 29/240.5 |
| 2,254,620 A | 9/1941 | Miller | |
| 2,316,297 A | 4/1943 | Southerland et al. | |
| 2,371,978 A | 3/1945 | Perham | |
| 2,453,227 A | 11/1948 | James | |
| 2,583,625 A | 1/1952 | Bergan | |

(Continued)

FOREIGN PATENT DOCUMENTS

| | | |
|---|---|---|
| AU | 2003297432 | 7/2004 |
| CA | 2 339 060 | 2/2000 |

(Continued)

OTHER PUBLICATIONS

Derwent-Acc-No. 1978-B8090A "Hand tool for forming telephone connections—comprises pliers with reciprocably driven ram crimping clip around conductors against anvil".

(Continued)

*Primary Examiner* — Corrine M McDermott
*Assistant Examiner* — Mark Mashack
(74) *Attorney, Agent, or Firm* — Workman Nydegger; Randy Shen

(57) ABSTRACT

The present invention relates to closing an opening within a subcutaneous bodily vessel by using a spiral closure device to engage tissue around the opening. The spiral closure device is adapted to be threaded into the vessel wall surrounding the opening in the bodily vessel. A deployment mechanism may be used to rotate the spiral closure device. As the deployment mechanism is rotated the spiral closure device is rotated such that a tip of the spiral closure device engages the vessel wall around the opening in the bodily vessel. Continued rotation of the spiral closure device threads the closure device through the tissue around the opening. As the distal end is threaded through the vessel wall, the narrowing closure device pulls the vessel wall tissue together, thereby effectively closing the opening.

12 Claims, 3 Drawing Sheets

(56) References Cited

U.S. PATENT DOCUMENTS

| | | | |
|---|---|---|---|
| 2,684,070 A | | 7/1954 | Kelsey |
| 2,755,699 A | * | 7/1956 | Forster .................. 411/438 |
| 2,910,067 A | | 10/1959 | White |
| 2,944,311 A | | 7/1960 | Schneckenberger |
| 2,951,482 A | | 9/1960 | Sullivan |
| 2,969,887 A | | 1/1961 | Darmstadt et al. |
| 3,015,403 A | | 1/1962 | Fuller |
| 3,113,379 A | | 12/1963 | Frank |
| 3,120,230 A | | 2/1964 | Skold |
| 3,142,878 A | | 8/1964 | Santora |
| 3,209,754 A | | 10/1965 | Brown |
| 3,348,595 A | | 10/1967 | Stevens, Jr. |
| 3,357,070 A | | 12/1967 | Sloan |
| 3,482,428 A | | 12/1969 | Kapitanov et al. |
| 3,494,533 A | | 2/1970 | Green et al. |
| 3,510,923 A | | 5/1970 | Blake |
| 3,523,351 A | | 8/1970 | Filia |
| 3,586,002 A | | 6/1971 | Wood et al. |
| 3,604,425 A | | 9/1971 | Le Roy |
| 3,618,447 A | | 11/1971 | Goins |
| 3,677,243 A | | 7/1972 | Nerz |
| 3,682,180 A | | 8/1972 | McFarlane |
| 3,757,629 A | | 9/1973 | Schneider |
| 3,805,337 A | | 4/1974 | Branstetter |
| 3,823,719 A | | 7/1974 | Cummings |
| 3,828,791 A | | 8/1974 | Santos |
| 3,856,016 A | | 12/1974 | Davis |
| 3,874,388 A | | 4/1975 | King et al. |
| 3,908,662 A | | 9/1975 | Razgulov et al. |
| 3,926,194 A | | 12/1975 | Greenberg et al. |
| 3,939,820 A | | 2/1976 | Grayzel |
| 3,944,114 A | | 3/1976 | Coppens |
| 3,960,147 A | | 6/1976 | Murray |
| 3,985,138 A | | 10/1976 | Jarvik |
| 4,007,743 A | | 2/1977 | Blake |
| 4,014,492 A | | 3/1977 | Rothfuss |
| 4,018,228 A | | 4/1977 | Goosen |
| 4,047,533 A | | 9/1977 | Perciaccante et al. |
| 4,064,881 A | | 12/1977 | Meredith |
| 4,112,944 A | | 9/1978 | Williams |
| 4,153,321 A | | 5/1979 | Pombrol |
| 4,162,673 A | | 7/1979 | Patel |
| 4,169,476 A | | 10/1979 | Hiltebrandt |
| 4,189,808 A | | 2/1980 | Brown |
| 4,192,315 A | | 3/1980 | Hilzinger et al. |
| 4,201,215 A | | 5/1980 | Crossett et al. |
| 4,204,541 A | * | 5/1980 | Kapitanov .................. 606/145 |
| 4,207,870 A | | 6/1980 | Eldridge |
| 4,214,587 A | | 7/1980 | Sakura, Jr. |
| 4,215,699 A | | 8/1980 | Patel |
| 4,217,902 A | | 8/1980 | March |
| 4,267,995 A | | 5/1981 | McMillan |
| 4,273,129 A | | 6/1981 | Boebel |
| 4,274,415 A | | 6/1981 | Kanamoto et al. |
| 4,278,091 A | | 7/1981 | Borzone |
| 4,317,445 A | | 3/1982 | Robinson |
| 4,317,451 A | | 3/1982 | Cerwin et al. |
| 4,318,401 A | | 3/1982 | Zimmerman |
| 4,327,485 A | | 5/1982 | Rix |
| 4,345,606 A | | 8/1982 | Littleford |
| 4,368,736 A | | 1/1983 | Kaster |
| 4,396,139 A | | 8/1983 | Hall et al. |
| 4,407,286 A | | 10/1983 | Noiles et al. |
| 4,411,654 A | | 10/1983 | Boarini et al. |
| 4,412,832 A | | 11/1983 | Kling et al. |
| 4,428,376 A | | 1/1984 | Mericle |
| 4,440,170 A | | 4/1984 | Golden et al. |
| 4,449,531 A | | 5/1984 | Cerwin et al. |
| 4,475,544 A | | 10/1984 | Reis |
| 4,480,356 A | | 11/1984 | Martin |
| 4,485,816 A | | 12/1984 | Krumme |
| RE31,855 E | | 3/1985 | Osborne |
| 4,505,273 A | | 3/1985 | Braun et al. |
| 4,505,274 A | | 3/1985 | Speelman |
| 4,523,591 A | | 6/1985 | Kaplan et al. |
| 4,523,695 A | | 6/1985 | Braun et al. |
| 4,525,157 A | | 6/1985 | Valaincourt |
| 4,526,174 A | | 7/1985 | Froehlich |
| 4,586,503 A | | 5/1986 | Kirsch et al. |
| 4,592,498 A | | 6/1986 | Braun et al. |
| 4,595,559 A | | 6/1986 | Fleischhacker |
| 4,596,559 A | | 6/1986 | Fleischhacker |
| 4,607,638 A | | 8/1986 | Crainich |
| 4,610,251 A | | 9/1986 | Kumar |
| 4,610,252 A | | 9/1986 | Catalano |
| 4,635,634 A | | 1/1987 | Santos |
| 4,651,737 A | | 3/1987 | Deniega |
| 4,664,305 A | | 5/1987 | Blake, III et al. |
| 4,665,906 A | | 5/1987 | Jervis |
| 4,687,469 A | | 8/1987 | Osypka |
| 4,693,249 A | | 9/1987 | Schenck et al. |
| 4,697,312 A | | 10/1987 | Freyer |
| 4,719,917 A | | 1/1988 | Barrows et al. |
| 4,724,840 A | | 2/1988 | McVay et al. |
| 4,738,658 A | | 4/1988 | Magro et al. |
| 4,744,364 A | | 5/1988 | Kensey |
| 4,747,407 A | | 5/1988 | Liu et al. |
| 4,759,364 A | | 7/1988 | Boebel |
| 4,771,782 A | | 9/1988 | Millar |
| 4,772,266 A | | 9/1988 | Groshong |
| 4,777,950 A | | 10/1988 | Kees, Jr. |
| 4,789,090 A | | 12/1988 | Blake, III |
| 4,832,688 A | | 5/1989 | Sagae et al. |
| 4,836,204 A | | 6/1989 | Landymore et al. |
| 4,852,568 A | | 8/1989 | Kensey |
| 4,860,746 A | | 8/1989 | Yoon |
| 4,865,026 A | | 9/1989 | Barrett |
| 4,874,122 A | | 10/1989 | Froelich et al. |
| 4,878,915 A | | 11/1989 | Brantigan |
| 4,885,003 A | | 12/1989 | Hillstead |
| 4,886,067 A | | 12/1989 | Palermo |
| 4,887,601 A | | 12/1989 | Richards |
| 4,890,612 A | | 1/1990 | Kensey |
| 4,902,508 A | | 2/1990 | Badylak et al. |
| 4,917,087 A | | 4/1990 | Walsh et al. |
| 4,917,089 A | | 4/1990 | Sideris |
| 4,929,240 A | | 5/1990 | Kirsch et al. |
| 4,934,364 A | | 6/1990 | Green |
| 4,950,258 A | | 8/1990 | Kawai et al. |
| 4,957,499 A | | 9/1990 | Lipatov et al. |
| 4,961,729 A | | 10/1990 | Vaillancourt |
| 4,976,721 A | | 12/1990 | Blasnik et al. |
| 4,983,176 A | | 1/1991 | Cushman et al. |
| 4,997,436 A | | 3/1991 | Oberlander |
| 4,997,439 A | | 3/1991 | Chen |
| 5,002,562 A | | 3/1991 | Oberlander |
| 5,007,921 A | | 4/1991 | Brown |
| 5,015,247 A | | 5/1991 | Michelson |
| 5,021,059 A | | 6/1991 | Kensey et al. |
| 5,026,390 A | * | 6/1991 | Brown .................. 606/221 |
| 5,030,226 A | | 7/1991 | Green et al. |
| 5,032,127 A | | 7/1991 | Frazee et al. |
| 5,047,047 A | | 9/1991 | Yoon |
| 5,053,008 A | | 10/1991 | Bajaj |
| 5,059,201 A | | 10/1991 | Asnis |
| 5,061,274 A | | 10/1991 | Kensey |
| 5,078,731 A | | 1/1992 | Hayhurst |
| 5,092,941 A | | 3/1992 | Miura |
| 5,100,418 A | | 3/1992 | Yoon et al. |
| 5,100,422 A | | 3/1992 | Berguer et al. |
| 5,108,420 A | * | 4/1992 | Marks .................. 606/213 |
| 5,108,421 A | | 4/1992 | Fowler |
| 5,114,032 A | | 5/1992 | Laidlaw |
| 5,114,065 A | | 5/1992 | Storace |
| 5,116,349 A | | 5/1992 | Aranyi |
| 5,122,122 A | | 6/1992 | Allgood |
| 5,122,156 A | | 6/1992 | Granger et al. |
| 5,131,379 A | | 7/1992 | Sewell, Jr. |
| 5,141,520 A | | 8/1992 | Goble et al. |
| 5,147,381 A | | 9/1992 | Heimerl et al. |
| 5,156,609 A | | 10/1992 | Nakao et al. |
| 5,163,343 A | * | 11/1992 | Gish .................. 81/120 |
| 5,167,634 A | | 12/1992 | Corrigan, Jr. et al. |
| 5,167,643 A | | 12/1992 | Lynn |

(56) References Cited

U.S. PATENT DOCUMENTS

| | | |
|---|---|---|
| 5,171,249 A | 12/1992 | Stefanchik et al. |
| 5,171,250 A | 12/1992 | Yoon |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Janota |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A * | 5/1994 | Welch .................. 128/898 |
| 5,318,542 A | 6/1994 | Hirsch et al. |
| 5,320,639 A | 6/1994 | Rudnick |
| 5,327,908 A | 7/1994 | Gerry |
| 5,330,445 A | 7/1994 | Haaga |
| 5,330,503 A * | 7/1994 | Yoon ..................... 606/223 |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| RE34,866 E | 2/1995 | Kensey et al. |
| 5,392,978 A | 2/1995 | Velez et al. |
| 5,395,030 A | 3/1995 | Kuramoto et al. |
| 5,404,621 A | 4/1995 | Heinke |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,478,352 A | 12/1995 | Fowler |
| 5,478,353 A | 12/1995 | Yoon |
| 5,478,354 A | 12/1995 | Tovey et al. |
| 5,486,195 A | 1/1996 | Myers et al. |
| 5,497,933 A | 3/1996 | DeFonzo et al. |
| 5,507,744 A | 4/1996 | Tay et al. |
| 5,507,755 A | 4/1996 | Gresl et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,582,616 A * | 12/1996 | Bolduc et al. .................. 606/143 |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs et al. |
| 5,634,936 A | 6/1997 | Linden et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,669,935 A | 9/1997 | Rosenman et al. |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,700,273 A | 12/1997 | Buelna et al. |
| 5,713,899 A | 2/1998 | Marnay et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,116 A * | 3/1998 | Rosenman .................... 606/151 |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,736 A | 4/1998 | Volk |
| 5,735,873 A | 4/1998 | MacLean |
| 5,749,826 A | 5/1998 | Faulkner |

(56) References Cited

U.S. PATENT DOCUMENTS

| | | |
|---|---|---|
| 5,752,966 A | 5/1998 | Chang |
| 5,755,726 A | 5/1998 | Pratt et al. |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A * | 9/1998 | Yoon ........................ 606/148 |
| 5,817,113 A | 10/1998 | Gifford, III et al. |
| 5,820,631 A * | 10/1998 | Nobles ........................ 606/213 |
| 5,827,298 A | 10/1998 | Hart et al. |
| 5,830,125 A | 11/1998 | Scribner et al. |
| 5,830,221 A * | 11/1998 | Stein et al. ................... 606/157 |
| 5,833,698 A | 11/1998 | Hinchliffe et al. |
| 5,843,167 A | 12/1998 | Dwyer et al. |
| 5,845,657 A | 12/1998 | Carberry et al. |
| 5,853,421 A | 12/1998 | Leschinsky et al. |
| 5,853,422 A * | 12/1998 | Huebsch et al. ............. 606/213 |
| 5,855,312 A | 1/1999 | Toledano |
| 5,858,082 A | 1/1999 | Cruz et al. |
| 5,860,991 A | 1/1999 | Klein et al. |
| 5,861,005 A | 1/1999 | Kontos |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A | 7/1999 | Taheri |
| 5,922,009 A | 7/1999 | Epstein et al. |
| 5,928,231 A | 7/1999 | Klein et al. |
| 5,928,251 A | 7/1999 | Aranyi et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,575 A | 9/1999 | Bolduc et al. |
| 5,951,576 A | 9/1999 | Wakabayashi |
| 5,951,589 A | 9/1999 | Epstein et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,976,161 A | 11/1999 | Kirsch et al. |
| 5,984,934 A | 11/1999 | Ashby et al. |
| 5,984,948 A | 11/1999 | Hasson |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,010,517 A * | 1/2000 | Baccaro ........................ 606/151 |
| 6,013,084 A | 1/2000 | Ken et al. |
| 6,015,815 A | 1/2000 | Mollison |
| 6,022,372 A | 2/2000 | Kontos |
| 6,024,750 A | 2/2000 | Mastri |
| 6,024,756 A | 2/2000 | Huebsch et al. |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A * | 5/2000 | Hobbs et al. ................. 623/1.18 |
| 6,063,085 A | 5/2000 | Tay et al. |
| 6,063,114 A | 5/2000 | Nash et al. |
| 6,071,300 A | 6/2000 | Brenneman et al. |
| 6,077,281 A | 6/2000 | Das |
| 6,077,291 A | 6/2000 | Das |
| 6,080,182 A * | 6/2000 | Shaw et al. .................... 606/213 |
| 6,080,183 A | 6/2000 | Tsugita et al. |
| 6,083,242 A | 7/2000 | Cook |
| 6,090,130 A | 7/2000 | Nash et al. |
| 6,095,155 A | 8/2000 | Criscuolo |
| 6,102,271 A | 8/2000 | Longo et al. |
| 6,110,184 A | 8/2000 | Weadock |
| 6,113,612 A | 9/2000 | Swanson et al. |
| 6,117,125 A | 9/2000 | Rothbarth et al. |
| 6,117,148 A | 9/2000 | Ravo |
| 6,117,157 A * | 9/2000 | Tekulve ........................ 606/200 |
| 6,117,159 A | 9/2000 | Huebsch et al. |
| 6,120,524 A | 9/2000 | Taheri |
| 6,126,675 A | 10/2000 | Schervinsky et al. |
| 6,136,010 A | 10/2000 | Modesitt et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,161,263 A | 12/2000 | Anderson |
| 6,165,204 A | 12/2000 | Levinson et al. |
| 6,171,277 B1 | 1/2001 | Ponzi |
| 6,171,329 B1 * | 1/2001 | Shaw et al. .................... 606/213 |
| 6,174,322 B1 | 1/2001 | Schneidt |
| 6,179,849 B1 | 1/2001 | Yencho et al. |
| 6,179,860 B1 | 1/2001 | Fulton, III et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,220,248 B1 | 4/2001 | Voegele et al. |
| 6,221,102 B1 | 4/2001 | Baker et al. |
| 6,231,561 B1 | 5/2001 | Frazier et al. |
| 6,245,079 B1 * | 6/2001 | Nobles et al. ................. 606/144 |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,302,898 B1 | 10/2001 | Edwards et al. |
| 6,305,891 B1 | 10/2001 | Burlingame |
| 6,309,416 B1 | 10/2001 | Swanson et al. |
| 6,319,258 B1 | 11/2001 | McAllen, III et al. |

(56) References Cited

U.S. PATENT DOCUMENTS

| | | | |
|---|---|---|---|
| 6,322,580 B1 | 11/2001 | Kanner | |
| 6,328,727 B1 | 12/2001 | Frazier et al. | |
| 6,329,386 B1 | 12/2001 | Mollison | |
| 6,334,865 B1 | 1/2002 | Redmond et al. | |
| 6,348,064 B1 | 2/2002 | Kanner | |
| 6,355,052 B1 | 3/2002 | Neuss et al. | |
| 6,358,258 B1 | 3/2002 | Arcia et al. | |
| 6,375,671 B1 * | 4/2002 | Kobayashi et al. | 606/213 |
| D457,958 S | 5/2002 | Dycus | |
| 6,383,208 B1 | 5/2002 | Sancoff et al. | |
| 6,391,048 B1 | 5/2002 | Ginn et al. | |
| 6,395,015 B1 | 5/2002 | Borst et al. | |
| 6,398,752 B1 | 6/2002 | Sweezer et al. | |
| 6,402,765 B1 | 6/2002 | Monassevitch et al. | |
| 6,409,739 B1 | 6/2002 | Nobles et al. | |
| 6,419,669 B1 | 7/2002 | Frazier et al. | |
| 6,421,899 B1 * | 7/2002 | Zitnay | 29/240.5 |
| 6,423,054 B1 | 7/2002 | Ouchi | |
| 6,425,911 B1 | 7/2002 | Akerfeldt et al. | |
| 6,428,472 B1 | 8/2002 | Haas | |
| 6,428,548 B1 | 8/2002 | Durgin et al. | |
| 6,443,158 B1 | 9/2002 | Lafontaine et al. | |
| 6,443,963 B1 | 9/2002 | Baldwin et al. | |
| 6,447,540 B1 | 9/2002 | Fontaine et al. | |
| 6,450,391 B1 | 9/2002 | Kayan et al. | |
| 6,458,130 B1 | 10/2002 | Frazier et al. | |
| 6,461,364 B1 | 10/2002 | Ginn et al. | |
| 6,482,224 B1 | 11/2002 | Michler et al. | |
| 6,488,692 B1 | 12/2002 | Spence et al. | |
| 6,500,115 B2 | 12/2002 | Krattiger et al. | |
| 6,506,210 B1 | 1/2003 | Kanner | |
| 6,508,828 B1 | 1/2003 | Akerfeldt et al. | |
| 6,514,280 B1 | 2/2003 | Gilson | |
| 6,517,555 B1 | 2/2003 | Caro | |
| 6,517,569 B2 | 2/2003 | Mikus et al. | |
| 6,527,737 B2 | 3/2003 | Kaneshige | |
| 6,533,762 B2 | 3/2003 | Kanner et al. | |
| 6,533,812 B2 | 3/2003 | Swanson et al. | |
| 6,537,288 B2 | 3/2003 | Vargas et al. | |
| 6,547,806 B1 | 4/2003 | Ding | |
| 6,551,319 B2 * | 4/2003 | Lieberman | 623/17.11 |
| 6,558,349 B1 | 5/2003 | Kirkman | |
| 6,569,173 B1 | 5/2003 | Blatter et al. | |
| 6,569,185 B2 | 5/2003 | Ungs | |
| 6,572,629 B2 | 6/2003 | Kalloo et al. | |
| 6,578,585 B1 | 6/2003 | Stachowski et al. | |
| 6,582,452 B2 | 6/2003 | Coleman et al. | |
| 6,582,482 B2 | 6/2003 | Gillman et al. | |
| 6,596,012 B2 | 7/2003 | Akerfeldt et al. | |
| 6,599,303 B1 | 7/2003 | Peterson et al. | |
| 6,602,263 B1 | 8/2003 | Swanson et al. | |
| 6,610,072 B1 | 8/2003 | Christy et al. | |
| 6,613,059 B2 | 9/2003 | Schaller et al. | |
| 6,613,060 B2 | 9/2003 | Adams et al. | |
| 6,616,686 B2 | 9/2003 | Coleman et al. | |
| 6,620,165 B2 | 9/2003 | Wellisz | |
| 6,623,509 B2 | 9/2003 | Ginn | |
| 6,623,510 B2 * | 9/2003 | Carley et al. | 606/213 |
| 6,626,918 B1 | 9/2003 | Ginn et al. | |
| 6,626,919 B1 | 9/2003 | Swanstrom | |
| 6,626,920 B2 | 9/2003 | Whayne | |
| 6,632,197 B2 | 10/2003 | Lyon | |
| 6,632,238 B2 | 10/2003 | Ginn et al. | |
| 6,634,537 B2 | 10/2003 | Chen | |
| 6,645,205 B2 | 11/2003 | Ginn | |
| 6,645,225 B1 | 11/2003 | Atkinson | |
| 6,645,255 B2 | 11/2003 | Atkinson | |
| 6,652,538 B2 | 11/2003 | Kayan et al. | |
| 6,652,556 B1 | 11/2003 | VanTassel et al. | |
| 6,663,633 B1 * | 12/2003 | Pierson, III | 606/148 |
| 6,663,655 B2 | 12/2003 | Ginn et al. | |
| 6,669,714 B2 | 12/2003 | Coleman et al. | |
| 6,673,083 B1 | 1/2004 | Kayan et al. | |
| 6,676,671 B2 | 1/2004 | Robertson et al. | |
| 6,676,685 B2 | 1/2004 | Pedros et al. | |
| 6,679,904 B2 | 1/2004 | Gleeson et al. | |
| 6,685,707 B2 | 2/2004 | Roman et al. | |
| 6,689,147 B1 | 2/2004 | Koster, Jr. | |
| 6,695,867 B2 | 2/2004 | Ginn et al. | |
| 6,699,256 B1 | 3/2004 | Logan et al. | |
| 6,702,826 B2 | 3/2004 | Liddicoat et al. | |
| 6,712,836 B1 | 3/2004 | Berg et al. | |
| 6,712,837 B2 | 3/2004 | Akerfeldt et al. | |
| 6,719,777 B2 | 4/2004 | Ginn et al. | |
| 6,726,704 B1 | 4/2004 | Loshakove et al. | |
| 6,736,822 B2 | 5/2004 | McClellan et al. | |
| 6,743,195 B2 | 6/2004 | Zucker | |
| 6,743,243 B1 | 6/2004 | Roy et al. | |
| 6,743,259 B2 | 6/2004 | Ginn | |
| 6,749,621 B2 | 6/2004 | Pantages et al. | |
| 6,749,622 B2 | 6/2004 | McGuckin et al. | |
| 6,755,842 B2 | 6/2004 | Kanner et al. | |
| 6,767,356 B2 | 7/2004 | Kanner et al. | |
| 6,776,785 B1 | 8/2004 | Yencho et al. | |
| 6,780,197 B2 | 8/2004 | Roe et al. | |
| 6,786,915 B2 | 9/2004 | Akerfeldt et al. | |
| 6,790,218 B2 * | 9/2004 | Jayaraman | 606/191 |
| 6,790,220 B2 | 9/2004 | Morris et al. | |
| 6,837,893 B2 * | 1/2005 | Miller | 606/139 |
| 6,837,906 B2 | 1/2005 | Ginn | |
| 6,846,319 B2 | 1/2005 | Ginn et al. | |
| 6,849,078 B2 | 2/2005 | Durgin et al. | |
| 6,860,895 B1 | 3/2005 | Akerfeldt et al. | |
| 6,890,343 B2 | 5/2005 | Ginn et al. | |
| 6,896,687 B2 | 5/2005 | Dakov | |
| 6,896,692 B2 | 5/2005 | Ginn et al. | |
| 6,904,647 B2 | 6/2005 | Byers, Jr. | |
| 6,913,607 B2 | 7/2005 | Ainsworth et al. | |
| 6,926,723 B1 | 8/2005 | Mulhauser et al. | |
| 6,926,731 B2 | 8/2005 | Coleman et al. | |
| 6,929,634 B2 | 8/2005 | Dorros et al. | |
| 6,942,641 B2 | 9/2005 | Seddon | |
| 6,942,691 B1 | 9/2005 | Chuter | |
| 6,964,668 B2 | 11/2005 | Modesitt et al. | |
| 6,969,397 B2 | 11/2005 | Ginn | |
| 6,984,238 B2 | 1/2006 | Gifford, III et al. | |
| 6,989,003 B2 | 1/2006 | Wing et al. | |
| 6,989,016 B2 | 1/2006 | Tallarida et al. | |
| 7,001,398 B2 | 2/2006 | Carley et al. | |
| 7,001,400 B1 | 2/2006 | Modesitt et al. | |
| 7,008,435 B2 | 3/2006 | Cummins | |
| 7,008,439 B1 | 3/2006 | Janzen et al. | |
| 7,025,776 B1 | 4/2006 | Houser et al. | |
| 7,033,379 B2 | 4/2006 | Peterson | |
| 7,060,084 B1 | 6/2006 | Loshakove et al. | |
| 7,063,711 B1 | 6/2006 | Loshakove et al. | |
| 7,074,232 B2 | 7/2006 | Kanner et al. | |
| 7,076,305 B2 | 7/2006 | Imran et al. | |
| 7,083,635 B2 | 8/2006 | Ginn | |
| 7,087,064 B1 | 8/2006 | Hyde | |
| 7,108,709 B2 | 9/2006 | Cummins | |
| 7,111,768 B2 | 9/2006 | Cummins et al. | |
| 7,112,225 B2 | 9/2006 | Ginn | |
| 7,144,411 B2 | 12/2006 | Ginn et al. | |
| 7,163,551 B2 | 1/2007 | Anthony et al. | |
| 7,169,158 B2 | 1/2007 | Sniffin et al. | |
| 7,169,164 B2 | 1/2007 | Borillo et al. | |
| 7,211,101 B2 | 5/2007 | Carley et | |
| 7,261,716 B2 | 8/2007 | Strobel et al. | |
| 7,306,614 B2 * | 12/2007 | Weller et al. | 606/151 |
| 7,311,720 B2 | 12/2007 | Mueller et al. | |
| 7,316,704 B2 | 1/2008 | Bagaoisan et al. | |
| 7,322,995 B2 | 1/2008 | Buckman et al. | |
| 7,326,230 B2 | 2/2008 | Ravikumar | |
| 7,331,979 B2 | 2/2008 | Khosravi et al. | |
| 7,335,220 B2 | 2/2008 | Khosravi et al. | |
| D566,272 S | 4/2008 | Walberg et al. | |
| 7,361,178 B2 | 4/2008 | Hearn et al. | |
| 7,361,183 B2 | 4/2008 | Ginn | |
| 7,361,185 B2 | 4/2008 | O'Malley et al. | |
| 7,393,363 B2 | 7/2008 | Ginn | |
| 7,396,359 B1 | 7/2008 | Derowe et al. | |
| 7,431,727 B2 | 10/2008 | Cole et al. | |
| 7,431,729 B2 | 10/2008 | Chanduszko | |

(56) References Cited

U.S. PATENT DOCUMENTS

| | | |
|---|---|---|
| 7,465,286 B2 | 12/2008 | Patterson et al. |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 | 1/2010 | Cosgrove et al. |
| D611,144 S | 3/2010 | Reynolds |
| 7,727,249 B2 | 6/2010 | Rahmani |
| 7,780,696 B2 | 8/2010 | Daniel et al. |
| 7,799,042 B2 | 9/2010 | Williamson, IV et al. |
| 7,806,904 B2 | 10/2010 | Carley et al. |
| 7,819,895 B2 | 10/2010 | Ginn et al. |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelov |
| 8,226,666 B2 | 7/2012 | Zarbatany et al. |
| 2001/0007077 A1 | 7/2001 | Ginn et al. |
| 2001/0031972 A1 | 10/2001 | Robertson et al. |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026215 A1 | 2/2002 | Redmond et al. |
| 2002/0026216 A1* | 2/2002 | Grimes ............ 606/213 |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0058960 A1 | 5/2002 | Hudson et al. |
| 2002/0072768 A1 | 6/2002 | Ginn |
| 2002/0077657 A1 | 6/2002 | Ginn et al. |
| 2002/0082641 A1 | 6/2002 | Ginn et al. |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0183786 A1* | 12/2002 | Girton ............ 606/213 |
| 2002/0183787 A1 | 12/2002 | Wahr et al. |
| 2002/0188318 A1 | 12/2002 | Carley et al. |
| 2002/0193808 A1* | 12/2002 | Belef et al. ............ 606/139 |
| 2002/0198562 A1 | 12/2002 | Ackerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0023248 A1 | 1/2003 | Parodi |
| 2003/0032981 A1 | 2/2003 | Kanner et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0097140 A1 | 5/2003 | Kanner |
| 2003/0109890 A1* | 6/2003 | Kanner et al. ............ 606/142 |
| 2003/0125766 A1 | 7/2003 | Ding |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2003/0208211 A1* | 11/2003 | Kortenbach ............ 606/151 |
| 2003/0233095 A1 | 12/2003 | Urbanski et al. |
| 2004/0009205 A1 | 1/2004 | Sawhney |
| 2004/0009289 A1 | 1/2004 | Carley et al. |
| 2004/0010285 A1 | 1/2004 | Carley et al. |
| 2004/0039414 A1 | 2/2004 | Carley et al. |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chanduszko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1* | 2/2005 | Jayaraman ............ 606/158 |
| 2005/0038500 A1 | 2/2005 | Boylan et al. |
| 2005/0059982 A1 | 3/2005 | Zung et al. |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0152949 A1 | 7/2005 | Hotchkiss et al. |
| 2005/0165357 A1 | 7/2005 | McGuckin et al. |
| 2005/0169974 A1 | 8/2005 | Tenerz et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228443 A1 | 10/2005 | Yassinzadeh |
| 2005/0234508 A1 | 10/2005 | Cummins et al. |
| 2005/0245876 A1 | 11/2005 | Khosravi et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0100664 A1 | 5/2006 | Pai et al. |
| 2006/0142784 A1 | 6/2006 | Kontos |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Carley et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerez |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2006/0287674 A1 | 12/2006 | Ginn et al. |
| 2006/0293698 A1 | 12/2006 | Douk |
| 2007/0005093 A1 | 1/2007 | Cox |

(56) References Cited

U.S. PATENT DOCUMENTS

| | | |
|---|---|---|
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0027525 A1 | 2/2007 | Ben-Muvhar |
| 2007/0049967 A1 | 3/2007 | Sibbitt, Jr. et al. |
| 2007/0049968 A1 | 3/2007 | Sibbitt Jr. et al. |
| 2007/0060895 A1 | 3/2007 | Sibbitt Jr. et al. |
| 2007/0060950 A1 | 3/2007 | Khosravi et al. |
| 2007/0060951 A1 | 3/2007 | Shannon |
| 2007/0083230 A1* | 4/2007 | Javois ............ 606/213 |
| 2007/0083231 A1 | 4/2007 | Lee |
| 2007/0112304 A1 | 5/2007 | Voss |
| 2007/0112365 A1 | 5/2007 | Hilal et al. |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0172430 A1 | 7/2007 | Brito et al. |
| 2007/0179527 A1 | 8/2007 | Eskuri et al. |
| 2007/0185530 A1 | 8/2007 | Chin-Chen et al. |
| 2007/0203506 A1 | 8/2007 | Sibbitt, Jr. et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green III et al. |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004636 A1 | 1/2008 | Walberg |
| 2008/0009794 A1 | 1/2008 | Bagaoisan et al. |
| 2008/0033459 A1 | 2/2008 | Shafi et al. |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0093414 A1 | 4/2008 | Bender et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287988 A1 | 11/2008 | Smith et al. |
| 2008/0300628 A1 | 12/2008 | Ellingwood |
| 2008/0312666 A1 | 12/2008 | Ellingwood et al. |
| 2008/0312686 A1 | 12/2008 | Ellingwood |
| 2008/0312740 A1 | 12/2008 | Wachter et al. |
| 2008/0319475 A1 | 12/2008 | Clark |
| 2009/0054912 A1 | 2/2009 | Heanue et al. |
| 2009/0105728 A1 | 4/2009 | Noda et al. |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0171388 A1 | 7/2009 | Dave et al. |
| 2009/0177212 A1 | 7/2009 | Carley et al. |
| 2009/0177213 A1 | 7/2009 | Carley et al. |
| 2009/0187215 A1 | 7/2009 | Mackiewicz et al. |
| 2009/0216267 A1 | 8/2009 | Willard et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0114156 A1 | 5/2010 | Mehl |
| 2010/0114159 A1 | 5/2010 | Roorda et al. |
| 2010/0130965 A1 | 5/2010 | Sibbitt Jr. |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0217132 A1 | 8/2010 | Ellingwood et al. |
| 2010/0249828 A1 | 9/2010 | Mavani et al. |
| 2011/0066163 A1 | 3/2011 | Cho et al. |
| 2011/0178548 A1 | 7/2011 | Tenerz |
| 2012/0035630 A1 | 2/2012 | Roorda |
| 2012/0245603 A1 | 9/2012 | Voss |
| 2012/0245626 A1 | 9/2012 | Ellingwood et al. |
| 2012/0310261 A1 | 12/2012 | Cummins et al. |
| 2013/0006274 A1 | 1/2013 | Walberg et al. |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |

(56) References Cited

FOREIGN PATENT DOCUMENTS

| | | |
|---|---|---|
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/62234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 11/427,297, Sep. 15, 2010, Office Action.
U.S. Appl. No. 11/767,818, Sep. 30, 2010, Office Action.
U.S. Appl. No. 12/365,397, Sep. 13, 2010, Office Action.
U.S. Appl. No. 10/356,214, Sep. 3, 2010, Notice of Allowance.
U.S. Appl. No. 10/435,104, Oct. 5, 2010, Notice of Allowance.
U.S. Appl. No. 10/682,459, Oct. 12, 2010, Office Action.
U.S. Appl. No. 11/406,203, Oct. 6, 2010, Issue Notification.
U.S. Appl. No. 11/532,576, Oct. 13, 2010, Notice of Allowance.
U.S. Appl. No. 11/958,281, Oct. 8, 2010, Office Action.
U.S. Appl. No. 12/114,031, Oct. 5, 2010, Office Action.
U.S. Appl. No. 12/403,277, Oct. 12, 2010, Office Action.
U.S. Appl. No. 11/508,715, Oct. 18, 2010, Office Action.
U.S. Appl. No. 60/693,531, filed Jun. 24, 2005, Carly.
U.S. Appl. No. 60/696,069, filed Jul. 1, 2005, Pantages et al.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/097,072, filed Sep. 15, 2008, Sibbitt Jr. et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 12/481,377, filed Jun. 9, 2009, Clark.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
Database WPI; Section PQ, Week 200120; Derwent Publications Ltd., London GB; AN 2001-203165; XP002199926 & ZA 200 100 528 A (Anthony T), Feb. 28, 2001 abstract.
Deepak Mital et al, Renal Transplantation Without Sutures Using The Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998,

(56) References Cited

OTHER PUBLICATIONS pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert Phd, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
Om Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Swee Lian Tan, MD, PHD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
Sy Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.
Ut Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.

(56) References Cited

OTHER PUBLICATIONS

U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Office Action.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, filed Aug. 17, 2010, Notice of Allowance.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/787,073, Sep. 15, 2010, Issue Notification.
U.S. Appl. No. 10/908,721, Oct. 19, 2006, Office Action.

(56) References Cited

OTHER PUBLICATIONS

U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/316,775, Apr. 16, 2008, Office Action.
U.S. Appl. No. 11/316,775, Aug. 6, 2008, Office Action.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/390,586, Jul. 6, 2010, Office Action.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/455,993, Feb. 17, 2009, Office Action.
U.S. Appl. No. 11/455,993, Dec. 16, 2009, Office Action.
U.S. Appl. No. 11/508,656, Dec. 9, 2009, Office Action.
U.S. Appl. No. 11/508,656, Mar. 25, 2010, Office Action.
U.S. Appl. No. 11/508,656, Aug. 30, 2010, Office Action.
U.S. Appl. No. 11/508,662, Dec. 28, 2009, Office Action.
U.S. Appl. No. 11/508,662, Apr. 14, 2010, Office Action.
U.S. Appl. No. 11/508,715, Jan. 6, 2010, Office Action.
U.S. Appl. No. 11/508,715, Apr. 26, 2010, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/675,462, Aug. 31, 2010, Office Action.
U.S. Appl. No. 11/744,089, Nov. 26, 2008, Office Action.
U.S. Appl. No. 11/744,089, Aug. 14, 2009, Office Action.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/852,190, Jun. 24, 2010, Office Action.
U.S. Appl. No. 11/958,281, Sep. 2, 2010, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,937, Mar. 30, 2009, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/402,398, Mar. 9, 2010, Office Action.
U.S. Appl. No. 12/402,398, May 20, 2010, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,277, Jul. 8, 2010, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 12/481,377, Jan. 3, 2012, Office Action.
U.S. Appl. No. 12/548,274, Dec. 28, 2011, Office Action.
U.S. Appl. No. 12/684,562, Dec. 28, 2011, Office Action.
U.S. Appl. No. 12/608,773, Jan. 7, 2003, Office Action.
U.S. Appl. No. 13/490,143, Jan. 4, 2013, Restriction Requirement.
U.S. Appl. No. 13/615,547, Jan. 18, 2013, Office Action.
U.S. Appl. No. 12/897,358, Jan. 12, 2012, Notice of Allowance.
U.S. Appl. No. 12/338,977, Jan. 19, 2012, Office Action.
U.S. Appl. No. 12/684,569, Jan. 27, 2012, Office Action.
U.S. Appl. No. 11/344,891, Jan. 22, 2013, Notice of Allowance.
U.S. Appl. No. 13/030,922, Jan. 31, 2013, Office Action.
U.S. Appl. No. 13/153,594, Jan. 29, 2013, Office Action.
U.S. Appl. No. 11/767,818, Feb. 3, 2012, Notice of Allowance.
U.S. Appl. No. 12/684,542, Jan. 30, 2012, Office Action.
U.S. Appl. No. 12/941,809, Jan. 30, 2012, Office Action.
U.S. Appl. No. 12/966,923, Feb. 3, 2012, Notice of Allowance.
U.S. Appl. No. 12/961,331, Feb. 1, 2013, Office Action.
U.S. Appl. No. 13/488,233, Feb. 5, 2013, Notice of Allowance.
U.S. Appl. No. 12/897,358, filed Oct. 4, 2010, Carley.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/961,331, filed Dec. 6, 2010, Voss.
U.S. Appl. No. 12/945,646, filed Nov. 12, 2010, Carley et al.
U.S. Appl. No. 12/966,923, filed Dec. 13, 2010, Cummins et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 13/017,636, filed Jan. 31, 2011, Carley et al.
U.S. Appl. No. 13/026,989, filed Feb. 14, 2011, Cummins.
U.S. Appl. No. 10/147,774, Dec. 2, 2010, Notice of Allowance.
U.S. Appl. No. 10/264,306, Oct. 29, 2010, Notice of Allowance.
U.S. Appl. No. 10/517,004, Nov. 23, 2010, Issue Notification.
U.S. Appl. No. 10/541,083, Dec. 1, 2010, Issue Notification.
U.S. Appl. No. 10/638,115, Dec. 22, 2010, Issue Notification.
U.S. Appl. No. 11/048,503, Dec. 8, 2010, Issue Notification.
U.S. Appl. No. 11/113549, Jan. 4, 2011, Office Action.
U.S. Appl. No. 11/198,811, Oct. 20, 2010, Issue Notification.
U.S. Appl. No. 11/852,190, Nov. 1, 2010, Office Action.

(56) References Cited

OTHER PUBLICATIONS

U.S. Appl. No. 11/959,334, Nov. 10, 2010, Issue Notification.
U.S. Appl. No. 12/106,928, Oct. 25, 2010, Office Action.
U.S. Appl. No. 12/113,851, Dec. 16, 2010, Office Action.
U.S. Appl. No. 12/114,031, Nov. 22, 2010, Office Action.
U.S. Appl. No. 12/114,091, Oct. 27, 2010, Restriction Requirement.
U.S. Appl. No. 12/114,091, Dec. 17, 2010, Office Action.
U.S. Appl. No. 12/402,398, Jan. 24, 2011, Office Action.
U.S. Appl. No. 12/403,256, Nov. 23, 2010, Issue Notification.
U.S. Appl. No. 12/945,646, Jan. 20, 2011, Office Action.
U.S. Appl. No. 12/608,769, Feb. 10, 2012, Office Action.
U.S. Appl. No. 12/684,400, Feb. 13, 2012, Office Action.
U.S. Appl. No. 12/724,304, Feb. 10, 2012, Office Action.
U.S. Appl. No. 10/264,306, Feb. 16, 2011, Issue Notification.
U.S. Appl. No. 11/767,818, Feb. 16, 2011, Office Action.
U.S. Appl. No. 10/667,144, Feb. 15, 2012, Issue Notification.
U.S. Appl. No. 12/135,858, Feb. 16, 2012, Office Action.
U.S. Appl. No. 12/945,646, Feb. 21, 2012, Notice of Allowance.
U.S. Appl. No. 12/143,020, Feb. 23, 2012, Notice of Allowance.
U.S. Appl. No. 12/548,274, Mar. 2, 2012, Office Action.
U.S. Appl. No. 12/642,319, Feb. 27, 2012, Office Action.
U.S. Appl. No. 13/030,922, filed Feb. 18, 2011, Cummins.
U.S. Appl. No. 13/039,087, filed Mar. 2, 2011, Palermo et al.
U.S. Appl. No. 10/356,214, Feb. 23, 2011, Issue Notification.
U.S. Appl. No. 11/852,190, Mar. 2, 2011, Office Action.
U.S. Appl. No. 12/122,603, Mar. 3, 2011, Office Action.
U.S. Appl. No. 11/958,281, Mar. 10, 2011, Office Action.
U.S. Appl. No. 11/532,576, Mar. 16, 2011, Issue Notification.
U.S. Appl. No. 11/396,731, Mar. 22, 2011, Office Action.
U.S. Appl. No. 11/427,297, Mar. 21, 2011, Office Action.
U.S. Appl. No. 12/114,031, Mar. 6, 2012, Office Action.
U.S. Appl. No. 12/684,470, Mar. 23, 2012, Office Action.
U.S. Appl. No. 12/688,065, Mar. 13, 2012, Office Action.
U.S. Appl. No. 12/897,358, Mar. 5, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 12/113,851, Mar. 29, 2012, Office Action.
U.S. Appl. No. 12/403,277, Apr. 3, 2012, Office Action.
U.S. Appl. No. 10/682,459, Apr. 1, 2011, Notice of Allowance.
U.S. Appl. No. 12/403,277, Mar. 31, 2011, Office Action.
U.S. Appl. No. 13/791,829, filed Mar. 8, 2013, Roorda et al.
U.S. Appl. No. 13/791,846, filed Mar. 8, 2013, Palermo.
U.S. Appl. No. 13/112,618, Mar. 29, 2013, Office Action.
U.S. Appl. No. 13/112,631, Mar. 29, 2013, Office Action.
U.S. Appl. No. 13/308,227, Apr. 10, 2013, Office Action.
U.S. Appl. No. 13/525,839, Apr. 1, 2013, Office Action.
U.S. Appl. No. 10/147,774, Apr. 6, 2011, Issue Notification.
U.S. Appl. No. 12/114,091, Apr. 5, 2012, Office Action.
U.S. Appl. No. 12/684,542, Apr. 16, 2012, Office Action.
U.S. Appl. No. 11/744,089, Apr. 15, 2013, Office Action.
U.S. Appl. No. 12/850,242, Apr. 18, 2013, Office Action.
U.S. Appl. No. 13/052,634, Feb. 8, 2013, Office Action.
U.S. Appl. No. 13/052,634, Apr. 22, 2013, Office Action.
U.S. Appl. No. 13/615,547, Apr. 12, 2013, Notice of Allowance.
U.S. Appl. No. 12/122,603, Apr. 22, 2011, Office Action.
U.S. Appl. No. 13/308,227, filed Nov. 30, 2011, Yibarren.
U.S. Appl. No. 12/688,065, Apr. 26, 2012, Office Action.
U.S. Appl. No. 11/396,141, Apr. 30, 2013, Office Action.
U.S. Appl. No. 11/852,190, Apr. 24, 2013, Office Action.
U.S. Appl. No. 12/848,642, Apr. 26, 2013, Office Action.
U.S. Appl. No. 13/490,143, Apr. 29, 2013, Notice of Allowance.
U.S. Appl. No. 12/113,851, Apr. 27, 2011, Office Action.
U.S. Appl. No. 12/481,377, Apr. 28, 2011, Office Action.
U.S. Appl. No. 12/114,031, May 11, 2011, Office Action.
U.S. Appl. No. 12/143,020, May 11, 2011, Office Action.
U.S. Appl. No. 11/344,891, May 15, 2013, Issue Notification.
U.S. Appl. No. 12/955,859, May 16, 2013, Office Action.
U.S. Appl. No. 13/488,233, May 15, 2013, Issue Notification.
U.S. Appl. No. 11/390,586, May 3, 2012, Notice of Allowance.
U.S. Appl. No. 12/684,400, May 9, 2012, Office Action.
U.S. Appl. No. 12/897,358, May 2, 2012, Issue Notification.
U.S. Appl. No. 12/966,923, May 16, 2012, Issue Notification.
U.S. Appl. No. 13/011,850, filed Jan. 21, 2011, Von Oepen et al.
U.S. Appl. No. 12/143,020, May 30, 2012, Issue Notification.
U.S. Appl. No. 12/393,877, May 21, 2012, Office Action.
U.S. Appl. No. 12/941,809, Jun. 1, 2012, Office Action.
U.S. Appl. No. 12/945,646, May 30, 2012, Issue Notification.
U.S. Appl. No. 12/973,204, May 30, 2012, Issue Notification.
U.S. Appl. No. 12/608,773, Jun. 7, 2012, Office Action.
U.S. Appl. No. 13/026,989, Jun. 8, 2012, Office Action.
U.S. Appl. No. 13/112,618, filed May 20, 2011, Gianotti et al.
U.S. Appl. No. 13/112,631, filed May 20, 2011, Voss.
U.S. Appl. No. 13/153,594, filed Jun. 6, 2011, Reyes et al.
U.S. Appl. No. 10/667,144, Jun. 6, 2011, Office Action.
U.S. Appl. No. 12/481,377, Jun. 21, 2011, Office Action.
U.S. Appl. No. 12/955,859, May 26, 2011, Office Action.
U.S. Appl. No. 12/114,091, Jul. 7, 2011, Office Action.
U.S. Appl. No. 12/945,646, Jul. 6, 2011, Office Action.
U.S. Appl. No. 13/525,839, filed Jun. 18, 2012, Carley et al.
U.S. Appl. No. 11/427,297, Jun. 26, 2012, Notice of Allowance.
U.S. Appl. No. 11/767,818, Jul. 4, 2012, Issue Notification.
U.S. Appl. No. 12/338,977, Jul. 11, 2012, Office Action.
U.S. Appl. No. 12/135,858, Jul. 13, 2011, Office Action.
U.S. Appl. No. 12/955,859, Jul. 21, 2011, Office Action.
U.S. Appl. No. 11/390,586, Jul. 18, 2012, Issue Notification.
U.S. Appl. No. 12/608,773, Jul. 20, 2012, Office Action.
U.S. Appl. No. 12/684,569, Jul. 30, 2012, Office Action.
U.S. Appl. No. 13/039,087, Jul. 17, 2012, Office Action.
U.S. Appl. No. 11/675,462, Aug. 3, 2011, Office Action.
U.S. Appl. No. 12/114,031, Aug. 2, 2011, Office Action.
U.S. Appl. No. 10/682,459, Aug. 10, 2011, Issue Notification.
U.S. Appl. No. 11/675,462, Aug. 16, 2012, Issue Notification.
U.S. Appl. No. 11/744,089, Aug. 8, 2012, Office Action.
U.S. Appl. No. 12/481,377, Aug. 10, 2012, Notice of Allowance.
U.S. Appl. No. 12/850,242, Aug. 6, 2012, Office Action.
U.S. Appl. No. 12/955,859, Aug. 6, 2012, Office Action.
U.S. Appl. No. 12/608,769, Aug. 22, 2012, Office Action.
U.S. Appl. No. 12/642,319, Aug. 28, 2012, Office Action.
U.S. Appl. No. 12/684,562, Aug. 21, 2012, Office Action.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 11/396,731, Sep. 1, 2011, Office Action.
U.S. Appl. No. 12/548,274, Sep. 10, 2012, Office Action.
U.S. Appl. No. 12/684,470, Aug. 30, 2012, Office Action.
U.S. Appl. No. 12/684,542, Sep. 13, 2012, Office Action.
U.S. Appl. No. 13/026,989, Sep. 16, 2011, Office Action.
U.S. Appl. No. 12/122,603, Sep. 23, 2011, Office action.
U.S. Appl. No. 12/393,877, Sep. 29, 2011, Office Action.
U.S. Appl. No. 12/402,398, Sep. 20, 2012, Office Action.
U.S. Appl. No. 12/688,065, Oct. 12, 2012, Office Action.
U.S. Appl. No. 12/848,642, Sep. 20, 2012, Office Action.
U.S. Appl. No. 12/987,792, Sep. 17, 2012, Office Action.
U.S. Appl. No. 10/667,144, Oct. 28, 2011, Notice of Allowance.
U.S. Appl. No. 12/945,646, Oct. 26, 2011, Office Action.
U.S. Appl. No. 11/427,297, Oct. 31, 2012, Issue Notification.
U.S. Appl. No. 12/114,091, Nov. 8, 2012, Office Action.
U.S. Appl. No. 12/403,277, Nov. 5, 2012, Office Action.
U.S. Appl. No. 12/608,769, Nov. 5, 2012, Notice of Allowance.
U.S. Appl. No. 12/684,400, Oct. 16, 2012, Office Action.
U.S. Appl. No. 12/848,642, Nov. 9, 2012, Office Action.
U.S. Appl. No. 12/850,242, Oct. 17, 2012, Office Action.
U.S. Appl. No. 13/039,087, Nov. 6, 2012, Notice of Allowance.
U.S. Appl. No. 12/338,977, Nov. 28, 2012, Office Action.
U.S. Appl. No. 12/961,331, Dec. 4, 2012, Office Action.
U.S. Appl. No. 13/030,922, Dec. 18, 2012, Office Action.
U.S. Appl. No. 12/393,877, Dec. 13, 2011, Office Action.
U.S. Appl. No. 12/941,809, Dec. 13, 2011, Restriction Requirement.
U.S. Appl. No. 12/955,859, Dec. 15, 2011, Office Action.
U.S. Appl. No. 12/402,398, Mar. 13, 2012, Notice of Allowance.
U.S. Appl. No. 12/684,470, Dec. 20, 2011, Restriction Requirement.
U.S. Appl. No. 12/684,569, Dec. 20, 2011, Restriction Requirement.
U.S. Appl. No. 11/675,462, Dec. 22, 2011, Notice of Allowance.

(56) References Cited

OTHER PUBLICATIONS

U.S. Appl. No. 13/898,202, filed May 20, 2013, Walberg et al.
U.S. Appl. No. 13/153,594, May 29, 2013, Office Action.
U.S. Appl. No. 13/791,829, May 29, 2013, Office Action.
U.S. Appl. No. 10/786,444, mailed Jul. 11, 2013, Notice of Allowance.
U.S. Appl. No. 11/344,891, mailed Jun. 26, 2013, Issue Notification.
U.S. Appl. No. 12/402,398, mailed Jun. 26, 2013, Issue Notification.
U.S. Appl. No. 13/525,839, mailed Jul. 15, 2013, Notice of Allowance.
U.S. Appl. No. 13/615,547, mailed Jul. 10, 2013, Issue Notification.
U.S. Appl. No. 10/908,721, mailed Jul. 18, 2013, Notice of Allowance.
U.S. Appl. No. 11/396,141, mailed Aug. 21, 2013, Office Action.
U.S. Appl. No. 11/744,089, mailed Aug. 8, 2013, Notice of Allowance.
U.S. Appl. No. 12/850,242, mailed Aug. 6, 2013, Notice of Allowance.
U.S. Appl. No. 12/955,859, mailed Aug. 1, 2013, Notice of Allowance.
U.S. Appl. No. 13/026,989, mailed Aug. 23, 2013, Office Action.
U.S. Appl. No. 13/030,922, mailed Jul. 18, 2013, Office Action.
U.S. Appl. No. 13/490,143, mailed Aug. 21, 2013, Issue Notification.
U.S. Appl. No. 13/615,547, mailed Aug. 7, 2013, Issue Notification.

* cited by examiner

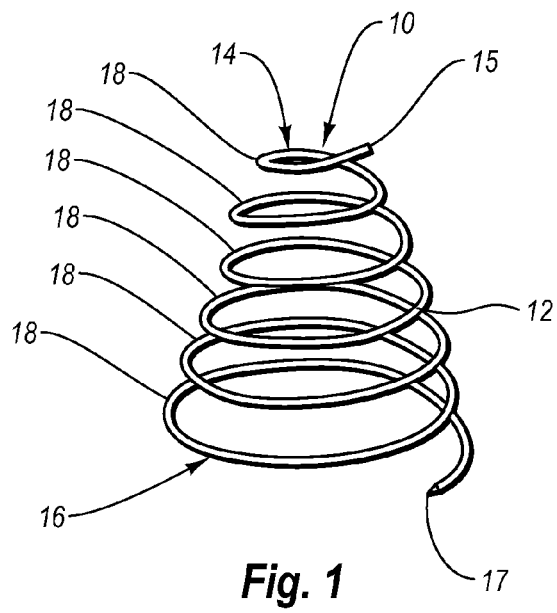
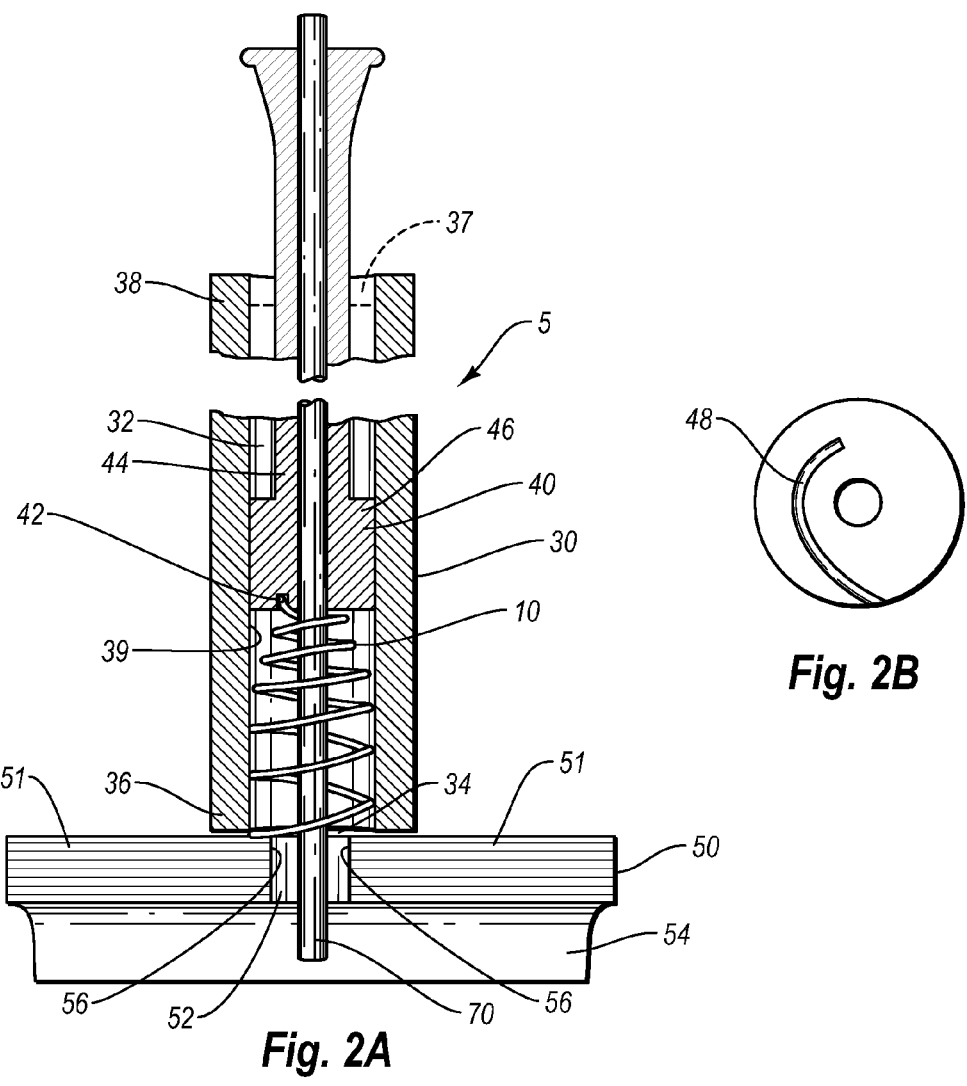

VESSEL CLOSURE DEVICE

BACKGROUND OF THE INVENTION

1. The Field of the Invention

Exemplary embodiments of the present invention generally relate to apparatus, systems and methods for closing an opening in a body vessel of a human or animal. More particularly, embodiments of the present invention generally relate to devices for engaging tissue around an opening in a body vessel formed during a percutaneous medical procedure, and to systems and methods for using such devices.

2. The Relevant Technology

One element in any medical procedure is the control and stoppage of blood loss. Stopping blood loss is a particular concern in intravascular medical procedures where a laceration in a vein or artery is made to grant venous or arterial access. Such procedures may be diagnostic or therapeutic in nature, and commonly involve, for example, the insertion, use, and removal of a catheter or stent to diagnose or treat a medical condition. During the procedure, an introducer sheath may allow introduction of various devices into the vessel while also minimizing blood loss during the procedure. Upon completion of the procedure, however, the devices and the introducer may be removed, thereby leaving a laceration or puncture in the vessel wall.

This laceration or puncture site is of particular concern in controlling the patient's blood loss. If the site is left unsealed, blood may escape and enter into the surrounding body cavities and tissue. Where excessive blood escapes, the effectiveness of the medical procedure may be compromised and complications may arise. To avoid or counter these complications, the medical staff must be vigilant in providing continued care to the patient following an intravascular procedure.

One method used to avoid excessive bleeding is to apply pressure to the affected area. This process attempts to block flow from the body vessel until the natural clotting process is complete. Pressure may be manually applied, or with a sandbag, bandage, or clamp. Moreover, the effectiveness of this pressure is compromised unless the patient remains nearly motionless while the pressure is applied. Patients are monitored during the time during which clotting is occurring, thereby also requiring much of a physician's or nurse's time. Typically, this natural process takes up to two hours; however, with other patients even more time may be required. The need for the patient to be immobilized can cause discomfort to the patient. In addition, the time for hemostasis potentially increases both the time during which the medical staff must monitor the patient as well as the patient's hospital stay, thus adding to the expense of the procedure.

Additional devices and techniques have been suggested to reduce the amount of time for hemostasis by percutaneously sealing a vascular opening by plugging, suturing and/or mechanically closing the puncture site. For example, collagen plugs are well known in the art. The collagen plug may be deployed into the vascular opening through an introducer sheath. When deployed, the blood or other body fluids cause the collagen plug to swell, such that it blocks the access site and provides hemostasis. Such devices may, however, be difficult to properly position in the vessel. Consequently, an improperly deployed plug may block the flow of fluid in the vessel, and/or be released into the blood stream where it can float downstream and potentially embolize.

Other mechanical devices or methods have been suggested for closing a puncture site. By way of example, a staple may be used. In one configuration, an "S" shaped staple includes barbs that may engage tissue on either side of the wound. Another staple may be ring-shaped and include barbs that project from the ring. Sides of the ring can be squeezed to separate the barbs, while the barbs may engage the tissue on either side of the wound. The sides can then be released, causing the barbs to return closer together, thereby also pulling the tissue closed over the wound. These staples, however, have a large cross-sectional profile and may not be easy to deliver through a percutaneous access site to close an opening in a vessel wall.

Accordingly, there remains a need for a vascular closure device which promotes rapid hemostasis and which can be easily positioned and deployed into a small access site to close an opening or puncture in a bodily vessel.

BRIEF SUMMARY OF THE INVENTION

Exemplary embodiments of the invention relate to a closure device for closing an access site in a bodily vessel following a percutaneous medical procedure. The closure device reduces the risk of bleeding following a medical procedure by improving the ability of medical personnel to quickly and easily close an access site of a blood vessel. The use of the closure device accelerates hemostasis in the patient, thus reducing the health risks associated with excess blood loss. Additionally, the vessel closure device allows a patient a near full range of motion soon after surgery, thus reducing the expenses of the procedure and corresponding hospital stay.

In one embodiment of the present invention, a vessel closure device includes a spiral clip. The spiral clip may be adapted to engage the tissue surrounding an opening in a bodily vessel, thereby pulling the tissue together and closing the opening. For example, the spiral clip may engage the walls of a blood vessel and pull the vessel walls together to close the opening. In some embodiments, the spiral clip can be a wire having a plurality of coils. Optionally, the spiral clip can be tapered such that one end of the clip can be wider than a second end of the clip. In another alternative, the medial portion of the clip may be wider than either end of the clip.

The spiral clip engages the vessel walls or other tissue when rotated. For example, the spiral clip may be a helically wound wire which, when rotated, extends into the vessel wall around the vascular opening. In other embodiments, the spiral clip can be a fastener with spiral threads, or a helical wire wound around a fastener, and grips the vessel walls when rotated. The spiral clip may be rotated by a deployment mechanism. The deployment mechanism may rotate in a first direction to facilitate engagement of the spiral clip with the tissue, or be rotated in a second direction to disengage the clip from the deployment mechanism. Optionally, the clip may be hollow or have an opening therein for receiving a vessel locator which can be positioned in the opening, through the clip, to determine the location of the opening in the bodily vessel so as to properly position the spiral clip.

In another embodiment, a system for closing an opening in a bodily vessel is described. Such system may include, for example, a spiral closure device and a deployment mechanism having an opening therein to receive the spiral closure device. The deployment mechanism can deploy the spiral closure device by rotably engaging the closure device to thereby close an opening in a bodily vessel. The spiral closure device may also be compressible to allow it to be received within the deployment mechanism. For instance, the closure device may be a tapered helical wire which has a natural shape that, at least in part, can be of a size that would not fit within the deployment mechanism but which, when compressed, can be received therein.

The deployment mechanism can, in some embodiments, include a tube in which the spiral closure device can be received. Further embodiments may also include a plunger within the tube, and such that the plunger traverses the tube along an axis of the tube and rotably engages the spiral closure device. The deployment mechanism may further be threaded to facilitate movement of the spiral closure device into the vascular opening. For example, a plunger may have external threads on its outer surface, while a tube has mating internal threads on an inner surface, such that as the plunger can be rotated, the plunger moves along an axis of the tube. In other embodiments, the inner surface of the tube has external threads and the outer surface of the plunger has internal threads. In yet another embodiment, a tube may have internal threads in which coils of a helical wire are received and such that as the spiral closure device can be rotated, it moves along the threads and along an axis of the tube.

A vessel closure system may also include a vessel locator for positioning the spiral closure device in the vascular opening. For example, a tube or other type of bleed-back device may be used. For instance, the bleed-back device can be inserted through the deployment mechanism and/or the spiral closure device. When the bleed-back device finds the vascular opening, it can be inserted into the lumen of the vessel such that blood or other bodily fluids are received in the device and flow through the device to exit at the distal end. This provides a visual indication to the medical personnel using the closure device that the vessel closure system is positioned for deployment. Upon viewing the fluid, and thereby determining that the locator and deployment mechanism are in place, the spiral closure device can be deployed and the vascular opening closed.

In other embodiments, a method for installing a vessel closure device is disclosed. The method can include, for example, locating the opening in the bodily vessel and positioning the deployment mechanism at the opening. Thereafter, and using the deployment mechanism, a spiral closure device can be deployed into the opening such that the spiral closure engages and pulls together the vessel wall tissue surrounding the opening. Locating the opening can further include extending a vessel locator through the deployment mechanism and/or closure device into a lumen of a bodily vessel and determining that fluid from the lumen is being received through the vessel locator.

The deployment mechanism can include a tube and a deployment member moving along an axis of the tubular receiving member. As such, using the deployment mechanism to rotably deploy the spiral closure device may include removably mounting the spiral closure device to the deployment member and rotating the deployment member such that rotating the deployment member moves it along the axis of the receiving member and causes the spiral closure device to rotably engage the vessel wall tissue.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope, nor are they necessarily drawn to scale. The invention will be described and explained with additional specificity and detail through the use of the accompanying drawings in which:

FIG. 1 illustrates a perspective view of a closure device in accordance with one embodiment of the invention;

FIG. 2A is partial cut-away view illustrating one embodiment of a system for closing an opening in a vessel wall using a spiral closure device;

FIG. 2B illustrates a bottom view of a deployment member having a retention sleeve or recess for receiving a spiral closure device;

DETAILED DESCRIPTION OF THE PREFERRED EMBODIMENTS

Figure 3:
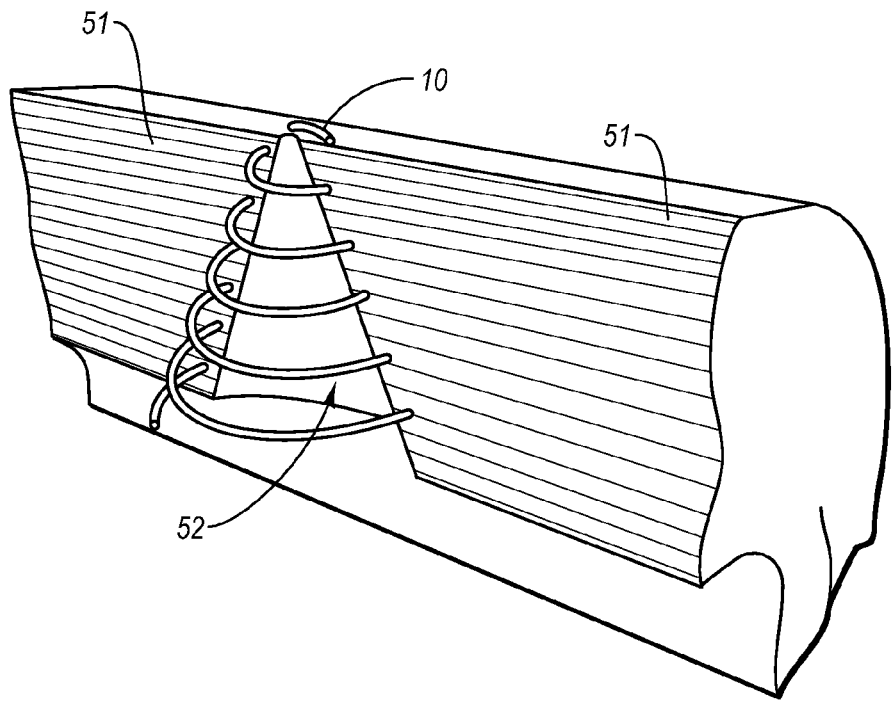
FIG. 3 illustrates the vessel wall of FIG. 2A after deployment of a spiral closure device to close an opening in the wall, according to one embodiment of the invention.

Exemplary embodiments of the present invention include delivery of a closure device for closing an opening or other laceration or puncture in the wall of a bodily vessel, thereby promoting hemostasis. When inserted into a vessel wall, the vessel closure device improves patient safety by drawing the vessel wall together, thereby reducing or eliminating leakage from the blood vessel into the surrounding tissue. The vessel closure device may be useful for a variety of medical procedures accessing blood vessels or other bodily vessels such as, for example, bodily cavities or bodily organs. The use of a closure device according to embodiments of the present invention can improve patient safety while also being capable of quick and efficient positioning and installation.

Referring now to FIG. 1, an exemplary embodiment of a vessel closure device 10 is illustrated. In the illustrated embodiment, vessel closure device 10 comprises a wire 12 wound in a helical shape such that it has a spiral configuration. More specifically, wire 12 is wound such that it has a plurality of coils 18. In this illustrated embodiment, coils 18 are substantially parallel, although it will be appreciated in light of this disclosure that this is not necessary and coils 18 can have any of a variety of configurations. For example, and not by way of limitation, vessel closure device 10 may include a second wire such that a double-helix is formed, and in which the coils of the second wire are perpendicular to the coils of the first wire. Further, the spacing or pitch between adjacent coils 18 of the wire 12 can be equidistant, different spacing, or combinations of equal or different spacings.

Vessel closure device 10 may also have any number of coils or any of a variety of shapes and configurations. For example, in the illustrated embodiment, wire 12 is wound such that vessel closure device 10 is substantially conical. More particularly, when viewed from above or below, coils 18 of vessel closure device 10 are generally circular in shape, and gradually reduce in size from distal end 16 to proximal end 14. In this manner, the diameter of a coil adjacent proximal end 14 is less than the diameter of a coil at distal end 16.

As discussed in more detail hereafter, one feature of a tapered configuration on vessel closure device 10 is the ability of vessel closure device 10 to effectively close an opening in a vessel wall. In particular, distal tip 17 can enter the vessel wall and coils 18 can thereafter be threaded around an opening in the vessel. As threading continues, the more narrow coils of vessel closure device 10 engage the vessel wall tissue and pull the wall together, thereby closing the opening.

Although a tapered configuration to vessel closure device 10 is illustrated, it will be understood by those skilled in the art that other configurations are possible and the illustrative nature of the exemplary embodiment should not be considered limiting to the various other configurations that are possible. For example, wire 12 may be wound in any number of manners. For instance, wire 12 may be wound such that vessel closure device 10 has a generally cylindrical shape, with or without a taper, or other configurations having only a portion of the device being tapered. Moreover, it is not necessary that the coils have a generally circular shape. For example, coils 18 may wound in any other regular or irregular geometric shape. By way of representation, the shape of one or more of coils 18 may be generally oval, diamond, trapezoidal, or the like.

Moreover, the cross-sectional shape and configuration of wire 12 is not limited to any particular design. For example, while wire 12 may have a substantially circular or elliptical cross-sectional shape, this feature is not limiting. For instance, in other embodiments, wire 12 has other cross-sectional shapes, such as but not limited to, triangular, square, diamond-shaped, and trapezoidal cross-sections.

Now referring to FIG. 2A, a system and method for installing vessel closure device 10 is illustrated and described in greater detail. As illustrated, one embodiment of a vessel closure system 5 is located at an opening 52 in a bodily vessel 50, and adapted to close opening 52 to prevent fluid loss from a lumen 54 of vessel 50. In this embodiment, vessel closure system 5 can include a delivery mechanism, including a delivery shaft 30 and a deployment member 40 disposed within delivery shaft 30, and vessel closure device 10 for closing opening 52.

Vessel closure device 10 may also be disposed within, and received by, delivery shaft 30. In particular, in this exemplary embodiment, delivery shaft 30 includes a chamber 32 extending from a proximal end 38 toward a distal end 36 of delivery shaft 30. For instance, in one configuration the chamber 32 runs along the length of delivery shaft 30. Chamber 32 is configured, in this embodiment, to receive both delivery shaft 30 and vessel closure device 10. For instance, chamber 32 may have a cross-sectional shape or configuration generally corresponding to the cross-sectional shape of deployment member 40, and slightly larger than deployment member 40. Accordingly, deployment member 40 can be easily inserted into chamber 32.

In other embodiments, however, chamber 32 can have a size about equal to or slightly less than the size of at least a portion of deployment member 40. In such embodiments, a seal and/or compression fit can be formed between deployment member 40 and the internal surface 39 of delivery shaft 30 which surrounds chamber 32. By forming a compression fit and/or seal within chamber 32, closure system 5 can act to restrict passing fluid along the length of delivery shaft 30. For instance, fluid that collects in the portion of delivery shaft 30 which is adjacent vessel 50 can be prevented from passing through delivery shaft 30 to the medical personnel operating closure system 5.

It will be understood that the mounting or mating of deployment member 40 with delivery shaft 30 can occur in various other manners. For instance, in another configuration, one or more mechanical seals, such as but not limited to, O-rings, can be mounted to a portion of deployment member 40 and be disposed between deployment member 40 and internal surface 39 of delivery shaft 30 and prevent fluid passing through delivery shaft 30.

In addition to or alternatively to creating a seal between deployment member 40 and internal surface 39 of delivery shaft 30, closure system 5 can include a seal 37 mounted to proximal end 38 of delivery shaft 30. This seal 37 can be one of a variety of different seals, including optionally being self sealing once it is inserted into proximal end 38 of delivery shaft 30. The seal 37, for example, may have an elastomeric body, such as silicone rubber or other material, with at least one slit and/or other collapsible opening formed therein to allow movement of deployment member 40. The collapsible openings or other portions of the seal 37 maintain a fluid tight seal with or against deployment member 40. Thus, blood or other bodily fluids are prevented from leaking out, and unwanted air is prevented from entering into the body. Examples of such flexible membranes or seals which can be utilized with the present invention are shown in U.S. Pat. Nos. 4,798,594, 5,176,652, and 5,453,095 the entireties of which are herein incorporated by reference.

In the illustrated embodiment, deployment member 40 can be disposed within chamber 32 and can be further configured to mount vessel closure device 10 to vessel 50 and thereby close opening 52. For example, in this embodiment, deployment member 40 can include a first, mounting portion 46 and a second, rotation portion 44. Mounting portion 46 has, in this embodiment, a generally circular cross-section and a diameter about equal to the diameter of the cross-section of chamber 32, and is further disposed within channel 32. In contrast, rotation portion 44 has a diameter less than the diameter of mounting portion 46.

Mounting portion 46 is, in this embodiment, adapted to engage vessel closure device 10, such that it can be secured within channel 32. For instance, mounting portion 46 may include a retention sleeve or recess 42 through which a proximal tip 15 (FIG. 1) of proximal end 14 can be inserted. Retention sleeve or recess 42, which is shown in more detail in FIG. 2B and without vessel closure device 10, can retain proximal end 14 in any suitable manner. For instance, sleeve or recess 42 can include a curved channel 48 having a shape generally corresponding to the helical shape of proximal end 14 of vessel closure device 10. Accordingly, curved channel 48 can be ramped or inclined along its length such that it approximates the shape contour of vessel closure device 10 at proximal end 14. In other embodiments, curved channel 48 may not be ramped along its length. For instance, all or a portion of the length of curved channel 48 may be substantially horizontal. In this manner, as proximal end 14 of vessel closure device 10 is inserted into curved channel 48, proximal end 14 is compressed and frictionally retained within retention sleeve or recess 42.

In light of the disclosure herein, it should be appreciated that any number of other mechanisms or retention devices may be used to engage vessel closure device 10 or otherwise secure vessel closure device 10 within channel 32. For instance, mounting portion 46 may be temporarily or permanently charged such that a magnetic field is created. Vessel closure device 10 may further be made of a ferrous material, or include a ferrous material portion or a coating of ferrous material, and attracted to mounting portion 46 by the magnetic field or be charged with an opposite charge. In other embodiments, mounting portion 46 may include a clasp for receiving proximal end 14. It will also be understood that combinations of the above are also possible.

Rotation portion 44 can be connected to mounting portion 46. Rotation portion 44 may, for example, be integrally formed with mounting portion 46 or otherwise directly or indirectly connected thereto. In some embodiments, rotation portion 44 can be configured to be rotated by the medical personnel using closure system 5 to position vessel closure device 10. By rotating rotation portion 44, such as grasping a portion of a proximal portion of the rotation portion 44, the medical personnel also rotates mounting portion 44 as well as vessel closure device 10.

Rotational motion of rotating vessel closure device 10 causes distal end 16 of vessel closure device 10 to engage the vessel wall tissue 51 surrounding opening 52. Moreover, by rotating deployment member 30, the medical personnel can cause deployment member 30 to move along the axis of chamber 32 in a direction toward vessel 50. Correspondingly, rotation of deployment member 30 causes vessel closure device 10 to rotate and move along the axis of chamber 32. In this manner, and as discussed in more detail hereafter, as rotation portion 44 is rotated, vessel closure device 10 is threaded into vessel wall 51 around opening 52. Thus, deployment member 40 can act as a plunger or piston within delivery shaft 30 by rotably pushing vessel closure device 10 into opening 52.

Although FIG. 2A illustrates mounting portion 46 and rotation portion 44 as having differing sizes, in light of the disclosure herein it should be appreciated that this feature is not limiting. For instance, mounting portion 46 and rotation portion 44 may be integrally formed as a shaft in which each portion has the same cross-sectional shape and the same size. It should be noted that the mounting portion 46 can have a configuration similar to the interior diameter or configuration of the chamber 32 or a configuration enables slidable and/or rotatable cooperation between the mounting portion 46 and the chamber 32.

With continued reference to FIG. 2A, it will be seen that to deploy vessel closure device 10 and thereby close opening 52, vessel closure device 10 may, in some embodiments, be flexible. This feature may be desirable for a number of reasons. For example, the width or diameter of channel 32 may be less than the width or diameter of one or more coils of vessel closure device 10. In such a case, a flexible vessel closure device 10 allows the larger width portion or portions of vessel closure device 10 to be deformed so as to fit within channel 32.

In one embodiment, for example, vessel closure device 10, when in a natural state, is tapered such that a width at the distal end of the device is larger than the width at the proximal end. Where the width at the distal end is larger than channel 32, the distal end may be bent or otherwise deformed to fit within channel 32. Such deformation may, for example, compress the coils by reducing the width of one or more coils. In some embodiments, to reduce the width of the coils may further increase the length of vessel closure device 10.

Once vessel closure device 10 is positioned within channel 32, whether or not such positioning requires deformation of vessel closure device 10, deployment member 40 can engage vessel closure device 10 and/or be mounted thereto to deploy vessel closure device 10 into opening 52 in vessel walls 51. Such deployment of vessel closure device 10 into opening 52 may be caused in any suitable manner, including those described herein. For example, rotating deployment mechanism 40 to move deployment mechanism 40 along the interior of delivery shaft 30 rotates vessel closure device 10 into vessel walls 51. As deployment mechanism 40 rotates and translates, it rotates vessel closure device 10 and pushes it toward distal end 34 of delivery shaft 30. At distal end 34, distal tip 17 of vessel closure device 10 exits delivery shaft 30 and is pressed against vessel walls 51.

When distal tip 17 is pushed against vessel walls 51, it can enter into vessel walls 51 adjacent opening 52. Distal tip 17 can have any suitable configuration. For instance, distal tip 17 can be flat or blunt, rounded, or can have a sharpened tip or sharpened edges that extend to a sharpened tip, or can have any combination thereof. As should be appreciated in light of the disclosure herein, a sharpened distal tip 17 can facilitate entry of vessel closure device 10 into vessel 50. However, this feature is not limiting as the forces applied to vessel closure device 10 to cause its rotational and/or translational motion can also be sufficient to cause a blunt or rounded distal tip 17 to enter and engage vessel wall tissue 51.

As vessel closure device 10 continues to rotate and translate, distal tip 17 rotates around opening 52 and through vessel walls 51, and moves deeper into vessel walls 51. In effect, this provides a threading action and vessel closure device 10 can be threaded through vessel walls 51 surrounding opening 52. Accordingly, as this rotation and translation continues, proximal end 14 of vessel closure device 10 is also moved closer to, and can engage, vessel walls 10.

In some embodiments, such as where vessel closure device 10 is deformed when placed in the deployment mechanism comprising delivery shaft 30 and deployment member 40, vessel closure device 10 may change shape upon exiting distal end 34 of delivery shaft 30. For instance, where the width of a coil of the vessel closure device 10 has been compressed, the coil may return to its natural shape and size upon exiting delivery shaft 30. Accordingly, and by way of example, where vessel closure device 10 has a natural conical or tapered configuration, vessel closure device 10 may return to that natural shape when vessel closure device 10 is displaced from the deployment mechanism.

A variety of benefits may be obtained by deforming vessel closure device 10 to fit within delivery shaft 30 of a deployment mechanism and thereafter allowing vessel closure device 10 to return to its natural shape. For instance, where the deformation decreases the width or size of vessel closure device 10, a smaller delivery shaft 30 may be inserted into a patient beneath the skin. This allows a smaller incision to be used with the patient, thereby also decreasing the pain, recovery time, and scarring associated with the incision.

In addition, recapture of the natural shape of vessel closure device 10 can, in some embodiments, effectively close opening 52 in vessel walls 51 and bring portions of surface 56 of vessel walls 51 into together or towards each other. For instance, with reference now to FIG. 3, an exemplary embodiment of vessel closure device 10 deployed within and closing opening 52 is illustrated following removal of the deployment mechanism. In the illustrated embodiment, the height of vessel closure device 10 can be about equal to the thickness of the vessel walls 51 and the width of vessel closure device 10 can be slightly larger than the width of the opening in vessel 50. Accordingly, as vessel closure device 10 is inserted into the patient, it is secured to the vessel walls 51 accessible through opening 52, such as through surface 56, rather than the bodily tissue surrounding the vessel. Alternatively, the vessel closure device 10 can be secured to any portion of the vessel walls 51, whether or not through surface 56.

As will be appreciated in light of the disclosure herein, the illustrated configuration and size of vessel closure device 10 is not necessarily a limiting feature of the present invention. In particular, the size of vessel closure device 10 can be varied in any suitable manner as necessary for a particular application. For instance, vessel closure device 10 can be produced in any of various sizes suitable for a patient, medical procedure and/or body lumen which is being accessed.

As illustrated, vessel closure device 10 has a natural shape that is generally conical or tapered. The wider, distal end of vessel closure device 10 was first threaded into vessel walls 51 and vessel closure device 10 was thereafter threaded deeper into vessel walls 51. As vessel closure device 10 was threaded deeper into vessel walls 51, and the width of vessel closure device 10 becomes increasingly narrow, vessel closure device 10 continues to engage vessel wall tissue 51. As vessel closure device 10 narrows, it naturally pulls the tissue surrounding opening 52 together, thereby closing opening 52 or at least reducing the size of opening 52 to restrict the amount of fluid that can flow through opening 52.

To obtain these and other characteristics, in one embodiment, a closure device can be comprised of biocompatible materials that are at least temporarily deformable. Suitable biocompatible materials include, for example, superelastic materials (e.g., Nitinol). In addition, and by way of representation only, other suitable materials may include stainless steel, silver, platinum, tantalum, palladium, cobalt-chromium alloys, niobium, iridium, any equivalents thereof, alloys thereof or combinations thereof.

In addition, embodiments of a closure device may comprise a shape memory material. For example, the shape memory material can be shaped in a manner that allows deformation and restriction to induce a substantially tubular, linear orientation while within a delivery shaft, but can automatically retain the memory shape of the vessel closure device once extended from the delivery shaft. Shape memory materials have a shape memory effect in which they can be made to remember a particular shape. Once a shape has been remembered, the shape memory material may be bent out of shape or deformed and then returned to its original shape by unloading from strain or by heating. Typically, shape memory materials can be shape memory alloys ("SMA") comprised of metal alloys, or shape memory plastics ("SMP") comprised of polymers or shape memory metals ("SMM").

Usually, an SMA can have any non-characteristic initial shape that can then be configured into a memory shape by heating the SMA and confirming the SMA into the desired memory shape. After the SMA is cooled, the desired memory shape can be retained. This allows for the SMA to be bent, straightened, compacted, and placed into various contortions by the application of requisite forces; however, after the forces are released the SMA can be capable of returning to the memory or natural shape. The main types of SMAs include: copper-zinc-aluminum; copper-aluminum-nickel; nickel-titanium ("NiTi") alloys known as Nitinol; and cobalt-chromium-nickel alloys or cobalt-chromium-nickel-molybdenum alloys known as Elgiloy. However, other types of SMAs can be used. Typically, the nitinol and Elgiloy alloys can be more expensive, but have superior mechanical characteristics in comparison with the copper-based SMAs. The temperatures at which the SMA changes its crystallographic structure are characteristic of the alloy, and can be tuned by varying the elemental ratios For example, it is contemplated that the wire or one or more other materials forming a vessel closure device be comprised of a Ni-TI alloy that forms superelastic Nitinol. In the present case, Nitinol materials can be trained to remember a certain shape (e.g., a tapered or non-tapered helical coil). Thereafter, the materials can be deformed in the delivery shaft, an introducer, dilator, or some other tube, and then be released to return to its trained shape. Also, additional materials can be added to the Nitinol depending on the characteristics desired.

An SMP is a shape-shifting plastic that can be fashioned into a vessel closure device in accordance with the present invention. When an SMP encounters a temperature above the lowest melting point of the individual polymers, the blend can make a transition to a rubbery state. The elastic modulus can change more than two orders of magnitude across the transition temperature. As such, an SMP can be formed into a desired shape of a closure device by heating it above the transition temperature, fixing the SMP into the new shape, and cooling the material below the transition temperature. The SMP can then be arranged into a temporary shape by force, and then resume the memory shape once the force has been applied. Examples of SMPs include biodegradable polymers, such as oligo($\epsilon$-caprolactone)diol, oligo($\rho$-dioxanone) diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

For example, Veriflex™, the trade name for CRG's family of shape memory polymer resin systems, currently functions on thermal activation which can be customizable from $-20°$ F. to $520°$ F., which allows for customization within the normal body temperature. This allows a vessel closure device comprised of Veriflex™ to be inserted into a delivery shaft. Once unrestrained by the delivery shaft, the body temperature can cause the vessel closure device to spontaneously take its functional shape.

A vessel closure device made of a SMA, SMP, SMM or suitable superelastic material can be compressed or restrained in its delivery configuration on a delivery device using a sheath, delivery shaft, or similar restraint, and then deployed to its deployed configuration at a desired location by removal of closure device from the shaft. A vessel closure device made of a thermally sensitive material can be deployed by exposure of the closure device to a sufficient temperature to facilitate expansion.

In still other embodiments, the closure device is comprised at least partially of absorbent biomaterials. Suitable biomaterials include, for example, lyophilized or air-dried submucosal tissue or other extracellular matrix-derived tissue from warm-blooded vertebrate. Such materials have a variety of characteristics, including one or more of: biological remodeling, resistance to infection, and high similarity to autogenous material. Examples of such submucosal or other extracellular matrix-derived tissue is described in U.S. Pat. Nos. 4,902,508, 5,281,422, 5,573,784, 5,573,821, 6,206,931, and 6,790,220, the disclosures of which are herein expressly incorporated by reference.

A vessel closure device can include, for example, a coating of biomaterial around a wire core as described herein. As such a coating can have high similarity to autogenous material of the patient, there can be a reduced risk that the patient will reject the closure device or receive an infection. Moreover, biological remodeling characteristics of matrix-derived biomaterials can further foster regeneration of tissue around the closure device to close the opening in the bodily vessel and thereby prevent excess blood loss.

Returning now to FIG. 2A, one embodiment of vessel closure system 5 includes a vessel locator 70 for properly aligning and positioning vessel closure device 10 in opening 52. In one embodiment, for example, vessel locator 70 is a bleed-back device.

In the illustrated embodiment, vessel locator 70 is extended through the deployment mechanism, including delivery shaft 30 and deployment member 40. For instance, deployment member 30 may include a channel therethrough in which a bleed-back device or other suitable type of vessel locator 70 may be placed. Vessel locator 70 then extends through channel 32. Moreover, in some embodiments, vessel locator 70 may also extend through vessel closure device 10. For instance, in the illustrated embodiment where vessel closure device 10 is a helical coil, a void can be created within vessel closure device 10 through which vessel locator 70 extends. In light of the disclosure herein, it should be appreciated, however, that other configurations of a vessel closure device may allow for a vessel locator to extend therethrough, including, for example, the creation of a channel through an otherwise solid pin or connector. In still other embodiments, the vessel locator does not extend through the closure device. For instance, the closure device may be positioned adjacent the vessel locator.

To determine location of opening 52, the medical personnel operating closure system 5 can press locator 70 against vessel wall 51. Periodically, the medical personnel may move vessel locator 70 as they try to find opening 52. When vessel locator 70 is placed directly over opening 52, the medical personnel can extend vessel locator into the lumen 54 of bodily vessel 50. In exemplary embodiments, such as where vessel locator 70 is a bleed-back device, fluid in lumen 54 will flow into vessel locator 70, thereby allowing the medical personnel to view the bodily fluid and determine that vessel locator 70 has found opening 52.

Once vessel locator 70 has indicated that it is within opening 52, thereby also signaling that closure system 5 is properly positioned with respect to opening 52, vessel locator may, optionally, then be removed from lumen 54 and/or the deployment mechanism. Thereafter, vessel closure device 10 can be deployed into opening 52 in any suitable manner. For instance, vessel closure device 10 can be threaded into vessel walls 51 around opening 52 to engage wall tissue 51 and pull it together to close opening 52, as described herein, or installed in any other suitable manner.

Upon installation of vessel closure device 10, the deployment mechanism, including delivery shaft 30 and deployment member 40, can be retracted from bodily vessel 54 and removed from the incision in the patient. Prior to retraction and removal, however, the deployment mechanism may be disengaged or otherwise disconnected from vessel closure device 10. For instance, in the illustrated embodiment, deployment member 40 includes retention sleeve 42 in which the proximal tip of vessel closure device 10 is received. As deployment member 40 rotates in a first direction (e.g., counter-clockwise), deployment member 40 maintains its connection with vessel closure device 10 and moves within delivery shaft 30 towards vessel 50, such that the distal tip of vessel closure device 10 enters vessel wall 51.

If, however, deployment member 40 is rotated in a second direction (e.g., clockwise), deployment member 40 may translate along channel 32 away from vessel 50, and may detach from vessel closure device 10. In this manner, rotating deployment member in a first direction engages and installs vessel closure device 10, while rotation in a second direction detaches vessel closure device 10 from the deployment mechanism. Consequently, retention sleeve 42 is configured to temporarily and removably mount vessel closure device 10 to deployment member 40.

The rotational direction of deployment member 40 can be changed in any suitable manner. For example, medical personnel may manually rotate deployment member 40. In some embodiments, a ratchet mechanism, as is known in the art, may be used to facilitate the change of direction and/or rotation of deployment member 40. In addition, it should be appreciated, particularly in light of the disclosure herein, that no particular rotational direction or motion of deployment member 40 is limiting of the present invention. For instance, deployment member 40 may be rotated clockwise to install vessel closure device 10 and counter-clockwise to detach vessel closure device 10 from the deployment mechanism.

In other embodiments, vessel closure device 10 can be detached without rotating deployment member 40. For instance, as discussed herein, exemplary embodiments may include a clasp holding vessel closure device 10 to deployment member 40 or a magnetic field for mounting vessel closure device 10 to deployment member 40. In such embodiments, vessel closure device 10 may be detached by releasing the clasp or removing a magnetic field (e.g., by applying or removing an electrical charge or current).

Figure 4:
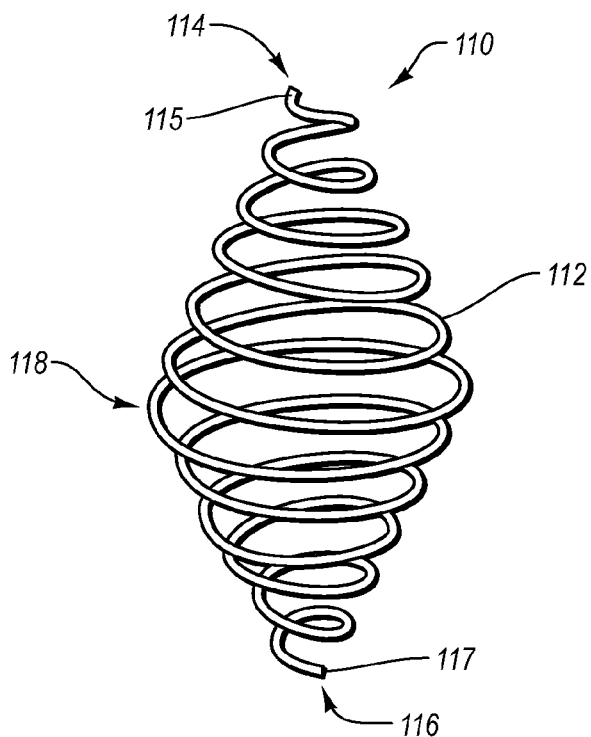
FIG. 4 illustrates an alternative embodiment of a vessel closure device.
Figure 5:
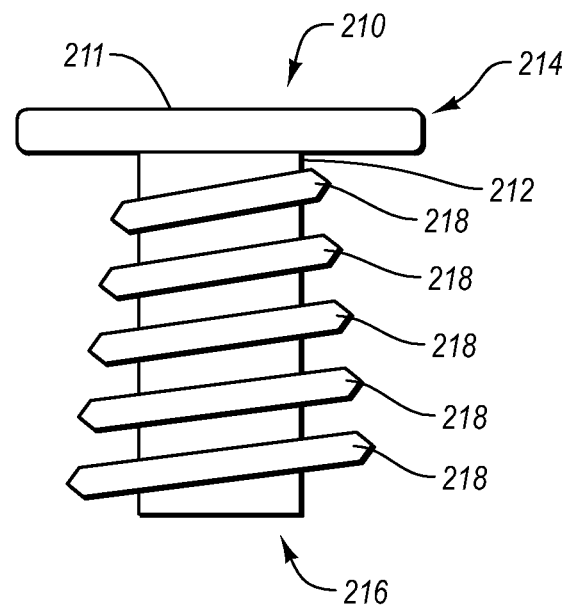
FIG. 5 illustrates a vessel closure device according to yet another embodiment of the present invention.

Turning now to FIGS. 4 and 5, various alternative embodiments of a spiral vessel closure device are illustrated. In FIG. 4, for example, a vessel closure device 110 is illustrated which has a beehive configuration or double tapered configuration. In particular, as illustrated, vessel closure device 110 comprises a wire 112 that is helically wound into a plurality of coils, wherein the coils take a double-conical, beehive configuration.

For example, vessel closure device 110 can include a first, proximal end 114 and a second distal end 116. Between proximal end 114 and distal end 116 is a medial portion 118. In the illustrated embodiment, the width of the coils at proximal end 114 and distal end 116 are less than the width of the coils at medial portion 118. In this manner, the width of vessel closure device 110 can increase between proximal end 114 and medial portion 118, and decrease between medial portion 118 and distal end 116.

As should be appreciated, particularly in light of the disclosure herein, vessel closure device 110 can be used to close an opening in any bodily vessel. For example, vessel closure device 110 can be deformed and placed inside a deployment mechanism such that in the closure system illustrated in FIG. 2A. In particular, vessel closure device 110 can be inserted into a delivery shaft and rotably deployed using engagement of a proximal tip 115 with the deployment mechanism, such that a distal tip 117 of a distal end 116 of vessel closure device 110 is pushed into a vessel wall. Vessel closure device 110 can then be further rotated and threaded into the vessel wall, around an opening therein, while the conical configuration allows vessel closure device 110 to pull the vessel wall together to thereby close off the vascular opening.

FIG. 5 illustrates yet another exemplary embodiment of a spiral vessel closure device. In the illustrated embodiment, a vessel closure device 210 can include a central post 212 around which a plurality of threads 218 are wound in a spiral manner. Optionally, at a proximal end 214 of vessel closure device 210, a cap 211 can be affixed to central post 212. Cap 211 can be configured to, for example, be temporarily and removably mounted to a deployment member so as to be rotably secured into the vessel wall around an opening in a bodily vessel.

Vessel closure device 210 can also be inserted to close the opening using a deployment mechanism similar to that illustrated in FIG. 2A. For example, vessel closure device 210 can be inserted into a delivery shaft while a deployment member engages cap 211 through cooperating structures, such as but not limited to, pins, tips, channels, hole, etc., and rotates, thereby also rotating vessel closure device 210 and translating it along the length of the delivery shaft. Upon exiting the shaft, the plurality of threads 218 engage the vessel wall around a vascular opening, thereby securing vessel closure device 210 to the vessel and also pulling the vessel wall together. Moreover, vessel closure device 210 can further act as a plug to not only pull the vessel wall together, but to also block the flow of fluid from the lumen of the bodily vessel.

In the illustrated embodiment, threads 218 are illustrated as being tapered. In particular, the threads nearest distal end 216 are longer than the threads nearest proximal end 214. It will be appreciated that such threads may be formed integrally with post 212, or may be separately formed. For instance, threads 218 may be formed of a single wire that is affixed to post 212.

In another embodiment, threads 218 may not be tapered, such that the diameter of each of threads 218 is equal. In still another embodiment, threads 218 may be of equal length while vessel closure device 210 is tapered. For instance, post 212 may be tapered while threads 218 have the same length, thereby providing a spiraling conical configuration having threads of the same length.

Figure 6:
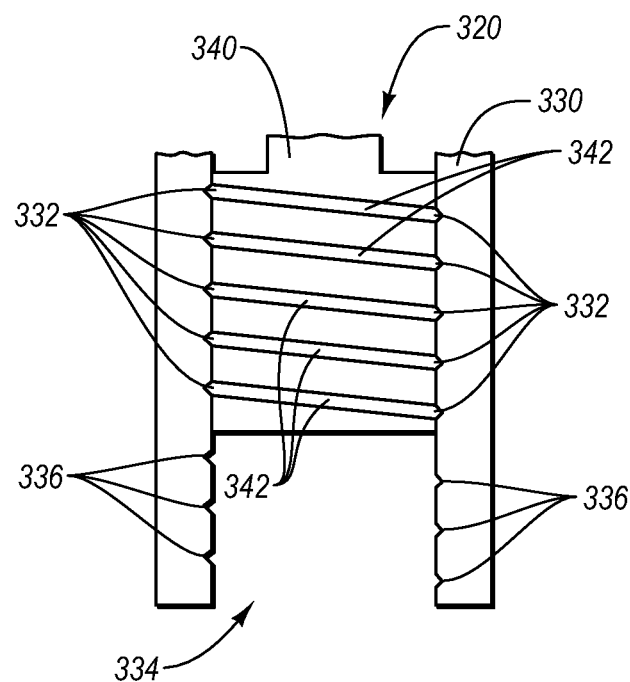
FIG. 6 illustrates an exemplary deployment mechanism for use in rotably deploying a spiral closure device according to one embodiment of the present invention.

Turning now to FIG. 6, an alternative embodiment of a deployment mechanism 320 is illustrated. In this embodiment, deployment mechanism 320 includes a delivery shaft 330 and a mating deployment member 340 for engaging a vessel closure device. Delivery shaft 330 may include internal threads 332 on the internal surface of the internal channel, while deployment member 340 has corresponding external threads 342 on the outer surface.

By including mating threads 332 and 342, a user can quickly and easily rotate deployment member 340 and also move deployment member 340 along the axis of delivery shaft 330. In particular, as deployment member 340 is rotated in one direction, threads 332, 342 cause deployment member 340 to translate and move along the axis of delivery shaft 330 towards a bodily vessel and the distal end 334 of delivery shaft 330. Conversely, when deployment member 340 is rotated in an opposing direction, threads 332, 342 cause deployment member 330 to translate and move along the axis of delivery shaft 330 away from distal end 334.

While threads 332 on delivery shaft 330 are illustrated as internal threads, and threads 342 on deployment member 340 are illustrated as external threads, it will be appreciated that this feature is exemplary only. In particular, threads of any type are contemplated. For example, in light of the disclosure herein, it should be appreciated that internal threads may be formed on the outer surface of the deployment member and mating external threads formed on the internal surface of delivery shaft 330.

In some embodiments, delivery shaft 330 may also include internal secondary threads 336 for receiving a closure device. Internal secondary threads may be used in addition to, or as an alternative to threads 332. In particular, a spiral vessel closure device, such as one having a plurality of threads or coils, can be set within the internal threads on the internal surface of delivery shaft 330. Thereafter, deployment member 330 can engage the closure device and be rotated—with or without threading—to rotate and translate the closure device into a vessel wall around a vascular opening.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A vessel closure system for engaging vessel wall tissue and closing an opening in a bodily vessel comprising:
    a spiral closure device having a tissue engaging portion and being configured to slide through the vessel wall tissue, said spiral closure device comprising a proximal end, a distal end with a sharpened distal tip, and a medial portion between said proximal end and said distal end, said medial portion being wider than said proximal end and said distal end, said spiral closure device having a double-conical configuration; and
    a deployment mechanism having an opening therein for receiving said spiral closure device, said deployment mechanism being configured to rotatably engage said spiral closure device to penetrate the vessel wall tissue with said sharpened distal tip and advance the vessel wall tissue along said length of the spiral closure device to thereby close an opening in a bodily vessel, said deployment mechanism comprising a vessel locator having a bleed-black lumen and extending through and beyond the distal end of said spiral closure device and configured for positioning said spiral closure device in said opening.

2. The vessel closure system as recited in claim 1, wherein said deployment mechanism is threaded to facilitate movement of said spiral closure device into said opening.

3. The vessel closure system as recited in claim 1, wherein said spiral closure device includes a helical wire comprising a plurality of coils, and wherein said spiral closure device is compressible to facilitate insertion into said deployment mechanism.

4. The vessel closure system as recited in claim 1, wherein said deployment mechanism comprises a tube for receiving said spiral closure device.

5. The vessel closure system as recited in claim 4, wherein said deployment mechanism further comprises:
    a plunger within said tube, wherein said plunger traverses said tube along an axis of said tube, and rotatably engages said spiral closure device.

6. The vessel closure system as recited in claim 4, wherein said spiral closure device is bio-absorbable.

7. A vessel closure system for engaging vessel wall tissue and closing an opening in a bodily vessel comprising:
    a spiral closure device having a first proximal end having a proximal tip, a second distal end having a sharpened distal tip configured to penetrate the vessel wall tissue, and a medial portion between said first proximal end and said second distal end, a portion of said medial portion being wider than said first proximal end and said second distal end, said spiral closure device having a double-conical pre-deployed configuration and a deployed, tissue penetrating configuration; and
    a deployment mechanism having an opening therein for receiving said spiral closure device, wherein said deployment mechanism rotatably engages said spiral closure device to penetrate the vessel wall tissue with said sharpened distal tip and advance the vessel wall tissue along said length of the spiral closure device to thereby close an opening in a bodily vessel, said deployment mechanism comprising a delivery shaft, a deployment member disposed within the delivery shaft and receiving said spiral closure device, and a vessel locator having a bleed-black lumen and extending through said delivery shaft, said deployment member configured for positioning said spiral closure device in said opening.

8. The vessel closure system as recited in claim 7, wherein said spiral closure device is configured to engage said tissue when rotated.

9. The vessel closure system as recited in claim 8, wherein said spiral closure device is configured to be threaded into said tissue.

10. The vessel closure system as recited in claim 7, wherein said spiral closure device engages said tissue when rotated in a first direction by said deployment mechanism, and disengages from said deployment mechanism when rotated in a second direction.

11. The vessel closure system as recited in claim 7, wherein said spiral closure device comprises a helically wound wire having a plurality of coils.

12. The vessel closure system as recited in claim 11, wherein said wire comprises a shape memory material.

* * * * *